(12) United States Patent
Ferdinando et al.

(10) Patent No.: US 7,381,428 B2
(45) Date of Patent: Jun. 3, 2008

(54) STABILIZED LANTHANUM CARBONATE COMPOSITIONS

(75) Inventors: Josephine Christine Ferdinando, Tadley (GB); Peter Neil Davies, Basingstoke (GB)

(73) Assignee: Shire International Licensing B.V. (NL)

( * ) Notice: Subject to any disclaimer, the term of this patent is extended or adjusted under 35 U.S.C. 154(b) by 0 days.

(21) Appl. No.: 11/272,569

(22) Filed: Nov. 9, 2005

(65) Prior Publication Data

US 2006/0121127 A1 Jun. 8, 2006

Related U.S. Application Data

(63) Continuation-in-part of application No. 10/926,330, filed on Aug. 26, 2004.

(60) Provisional application No. 60/497,560, filed on Aug. 26, 2003, provisional application No. 60/517,078, filed on Nov. 5, 2003.

(51) Int. Cl.
A61K 9/20 (2006.01)
A61K 31/28 (2006.01)
A61K 33/00 (2006.01)
A01N 59/00 (2006.01)
A01N 55/02 (2006.01)

(52) U.S. Cl. ............. 424/715; 424/464; 514/492; 514/960

(58) Field of Classification Search ............. 424/464, 424/715; 514/492, 960
See application file for complete search history.

(56) References Cited

U.S. PATENT DOCUMENTS

| | | | |
|---|---|---|---|
| 4,822,594 A | 4/1989 | Gibby | |
| 4,877,735 A | 10/1989 | Nogami et al. | |
| 5,853,758 A * | 12/1998 | Lo | 424/464 |
| 5,968,976 A | 10/1999 | Murrer et al. | |
| 6,703,005 B2 | 3/2004 | Allan et al. | |
| 2001/0014352 A1* | 8/2001 | Batra et al. | 424/464 |
| 2002/0051822 A1 | 5/2002 | Atherton et al. | |
| 2002/0155168 A1 | 10/2002 | Abrams et al. | |
| 2003/0186845 A1 | 10/2003 | Yoshida | |
| 2004/0029829 A1 | 2/2004 | Miyazaki et al. | |
| 2004/0043971 A1 | 3/2004 | Mazess et al. | |
| 2004/0120922 A1 | 6/2004 | Burke | |
| 2004/0161474 A1 | 8/2004 | Moerck et al. | |
| 2005/0096438 A1 | 5/2005 | Chang et al. | |
| 2005/0131138 A1 | 6/2005 | Connor et al. | |
| 2005/0147580 A1 | 7/2005 | Connor et al. | |
| 2005/0208080 A1 | 9/2005 | Heightman et al. | |
| 2005/0209423 A1 | 9/2005 | Chang et al. | |
| 2005/0220750 A1 | 10/2005 | Robert et al. | |
| 2005/0220751 A1 | 10/2005 | Charmot et al. | |
| 2005/0220889 A1 | 10/2005 | Charmot et al. | |
| 2005/0220890 A1 | 10/2005 | Charmot et al. | |
| 2005/0239901 A1 | 10/2005 | Chang et al. | |
| 2006/0121127 A1 | 6/2006 | Ferdinando et al. | |

FOREIGN PATENT DOCUMENTS

| | | |
|---|---|---|
| CA | 2 216 437 C | 10/1996 |
| EP | 295861 | 12/1988 |
| EP | 299910 | 1/1989 |
| EP | 1 267 662 A | 10/2001 |
| EP | 1 344 528 | 9/2003 |
| GB | 0015745 | 8/2000 |
| JP | 62-145024 | 6/1987 |
| JP | 62145024 | 6/1987 |
| JP | 1085088 A | 3/1989 |
| JP | 8070851 | 3/1996 |
| JP | 200247210 | 2/2002 |
| JP | 2002-187838 A | 7/2002 |
| JP | 2002-193735 A | 7/2002 |
| KR | 1998-0703280 | 6/2002 |
| WO | WO-96/30029 | 10/1996 |
| WO | WO-98/00104 A | 1/1998 |
| WO | WO-01/76409 A1 | 10/2001 |
| WO | WO-02/00227 | 1/2002 |
| WO | WO-02/49656 | 6/2002 |
| WO | WO-02/085348 A1 | 10/2002 |
| WO | WO-03/061624 | 7/2003 |
| WO | WO-03/094933 | 11/2003 |
| WO | WO-2004/016553 A2 | 2/2004 |
| WO | WO-2004/037274 | 5/2004 |
| WO | WO-2004/080467 | 9/2004 |
| WO | 2005/018651 | 3/2005 |
| WO | WO-2005/041902 | 5/2005 |
| WO | WO-2005/092039 | 10/2005 |
| WO | WO-2005/097072 | 10/2005 |

OTHER PUBLICATIONS

Marketletter Shire's Fosrenol clears bone safety hurdle Jun. 17, 2002, 1 page.*

Fukagawa Is Lanthanum carbonate safer and more effective than calcium carbonate for hyperphosphatemia in dialysis patients? Nature Clinical Practice nephrology 2005, 1(1), 20-21.*

(Continued)

*Primary Examiner*—John Pak
*Assistant Examiner*—Ernst Arnold
(74) *Attorney, Agent, or Firm*—Darby & Darby PC; Shelly M. Fujikawa

(57) ABSTRACT

Stabilized lanthanum carbonate compositions containing a monosaccharide or disaccharide stabilizing agent are disclosed. Subjects having hyperphosphatemia can be treated by administering a pharmaceutical composition containing a therapeutically effective amount of the stabilized lanthanum carbonate formulation.

12 Claims, 15 Drawing Sheets

OTHER PUBLICATIONS

U.S. Appl. No. 11/191,600, Ferdinando et al.

"Encyclopedia of Pharmaceutical Technology" by Swarbrick et al., vol. 2 (1990) "Biodegradable polyester polymers as drug carriers to clinical pharmaco-kinetics and pharmacodyanamics"; "Chewable tablets" pp. 397-417.

"Encyclopedia of Pharmaceutical Technology" by Swarbrick et al., Vo. 14 (1996); "Self-medication to technology transfer considerations for pharmaceuticals"; "Formulation design", pp. 385-400.

"Calcitriol, lanthanum carbonate, and other new phosphate binders in the management of renal osteodystrophy" by A. J. Hutchison, Perit Dial Int. vol. 19, Suppl. 2, 1999, pp. S408-S412.

International Search Report for PCT/CA2004/001563 mailed Jan. 19, 2005.

"Pharmaceutical Studies On Drug Delivery Systems For Geriatrics and Cancer Therapies", Yoshuinbobu Fukumori et al., Research and Development of Prophylactic and Therapeutic Agents for Age-Related Diseases in Aging Society. Annual Report 2002-2003, p. 281-285.

Preparation of Lecithin Microcapsules by a Dilution Method Using the Wurster Process for Intraarterial Administration in Gadolinium Neutron Capture Therapy, K. Jono et al., Chem Pharm Bull, 1999, vol. 47, No. 1, p. 54-63.

"Design and Preparation of Ethyl Cellulose Microcapsules of Gadopentetate Dimeglumine for Neutron-Capture Therapy Using the Wurster Process", Y. Fukumori et al., Chem Pharm Bull, 1993, vol. 41, No. 6, p. 1144-1148.

"Synthesis and FT-IR study of Ln-glucose-pyridine complexes", L. Zheng et al., AIP Conf. Proc. (1998), vol. 430, Number: Fourier Transform Spectroscopy, pp. 324-326.

"Interaction of metal ions with D-glucose in glassy state-a FT-IR study", Ning Xi et al., Proc. SPIE-Int. Soc. Opt. Eng., 1989, vol. 1145, Number: Int. Conf. Fourier Transform Spectrosc., 7th pp. 405-406.

"Interaction of Monosaccharides With Metal Ions—NMR Analysis Of Lanthanide Complex", Kunihiko Izumi, Kagaku Kogyo, 1988, vol. 39, No. 11, pp. 918-924.

"Fourier transform infrared spectroscopy as a tool for the study of rare earth carbohydrate complexes", Hong Liang et al. Mikrochim. Acta, 1988, vol. 1, No. 1-6, pp. 215-217.

NMR Studies of the interaction of metal ions with poly-(1, 4-hexuronates). V. Proton NMR spectra of methyl .alpha.-D-gluo- and methyl .beta.-Dhamamelopyranosides, 1, 6-anhydro-.beta.D-manno, 1,6-anhydro-.beta.-D-talo-and 1, 6-anhydro-.beta.-D-allopyranoses and epi-inositol, Hans Grasdalen et al., Acta Chem. Scand., Ser. A, 1978, vol. A32, No. 1, pp. 31-39.

"An analysis of NMR shifts in lanthanide complexes", H. Bergen et. al. Aust. J. Chem., 1977, vol. 30, No. 11, pp. 2361-2369.

Aqueous lanthanide shift reagents. 4. Interaction of praseodymium (3+), neodymium (3+), and europium (3+) ions with xylitol. Origin of induced shifts in polyols, Jacques Reuben, J. Am. Chem. Soc., 1977, vol. 99, No. 6, pp. 1765-1768.

"Stereospecific contact interactions in the nuclear magnetic resonance spectra of polyol-lanthanide complexes," Stephen J. Angyal et al., J. Chem. Soc., Chem. Commun., 1974, No. 15, pp. 589-590.

"NMR spectra of some sugar derivatives in the presence of rare-earth chelates", P. Girard et al., Tetrahedron, 1971, vol. 27, No. 23, pp. 5911-5920.

"NMR spectroscopy of (monosaccharides) in the presence of rare earth chelates", P. Girard et al., Bull. Soc. Chim. Fr., 1970, No. 12, pp. 4515-4516.

"Chemism of the reaction of neodymium and erbium ions with mono- and disaccharides" N.S. Poluektov et al., Zh. Neorg. Khim, 1970, vol. 15, No. 5, pp. 1203-1207.

"Reaction of neodymium and erbium ions with polyhydric alcohols and ascorbic acid", N.S. Poluektov et al., Ukr. Khim. Zh., 1970, vol. 36, No. 2, pp. 164-169.

"Nonradiative transfer of excitation energy between rare-earth ions in aqueous solution", F.S. Quiring, J. Chem. Phys., 1968, vol. 49, No. 5, pp. 2448-2449.

"Complexes of rare earth elements with disaccharides in solutions", N.P. Efryushina, et al., Zh. Neorg. Khim, 1967, vol. 12, No. 7, pp. 1855-1861.

"Complex rare earth compounds with sugars", N.P. Efryushina et al., Zh. Neorg. Khim, 1967, vol. 12, No. 4, pp. 933-938.

"Complexes of rare earth elements with some polyhydric alcohols", N.P. Efryushina, et al., Ukr. Khim. Zh. (Russ. Ed.), 1966, vol. 32, No. 10, pp. 1038-1043.

Limin Yang et al., "Interactions between metal ions and carbohydrates. Coordination behavior of neutral erythritol to Ca(II) and Lanthanide ions". Inorganic Chemistry, 42, 19, 5844-5856, Sep. 22, 2003.

"Lanthanide-saccharide chemistry: synthesis and characterisation of Ce (III)-saccharide complexes", A. Mukhopadhyay et al., Carbohydrate research (Netherlands) Jan. 29, 2000, 324 (1) p. 30-7.

"Homogeneous catalyst for DNA hydrolysis (4). Efficient DNA hydrolysis by lanthanide—saccharide complexes", J. Sumaoka et al., Nucleic acids symposium series (England) 1997, (37) p. 211-2.

"Calcium and pancreatic beta-cell function. IX. Demonstration of lanthanide-induced inhibition of insulin secretion independent of modifications in transmembrane Ca2+ fluxes.", P.R. Flatt et al., Endocrinology (United States) Oct. 1980, 107(4) p. 1007-13.

"Improved cell growth and total flavonoids of Saussurea medusa on solid culture medium supplemented with rare earth elements pharmaceutical production by herb plant callus culture", XF Yuan et al., Biotechnology Letters (24, 22, 1889-1892) 2002.

"Promotion of indole alkaloid production in Catharanthus roseus cell cultures by rare earth elements—the effect of cerium, yttrium and neodymium on ajmalicine and catharanthine production by'Vinca rosea", J. Zhao et al., Biotechnol. Lett. (22, 10, 825-28) 2000.

Simultaneous determination of ciprofloxacin and tetracycline in biological fluids based on dual-lanthanide sensitised luminescence using dry reagent chemical technology, R.C. Rodriguez-Diaz et al., Analytica Chimica Acta v 494 n 1-2 Oct. 8, 2003, p. 55-62.

Poluektov et al., Zh. Neorg. Khim, 1970, 15: 1995.

Bhogi B. Sheth et al., "Chapter :3, Compressed Tablets", Pharmaceutical Dosage Forms: Tablets, vol. 1, Marcel Dekker, Inc,: New York, 1980, pp. 109-185.

Ralph F. Shangraw, "Chapter :4, Compressed Tablets by Direct Compression", Pharmaceutical Dosage Forms: Tablets, vol. 1, Second Edition, Marcel Dekker, Inc.: New York, 1989, pp. 195-246.

Jahan B. Daruwala, "Chapter : 7, Chewable Tablets", Pharmaceutical Dosage Forms: Tablets, vol. 1, Marcel Dekker, Inc.: New York, 1980 pp. 289-337.

European Office Action dated Dec. 18, 2006 issued for corresponding European Patent Application No. 04761727.

De Broe, et al., "Lanthanum Carbonate: A new agent in the treatment of hyperphosphataemia in end-stage emal failure", Jun. 2002.

D'Haese et al., "A Multicenter study on the effects of lanthanum carbonate (Fosrenol) and calcium carbonate on renal bone disease in dialysis patients", Kidney International 2003, 63:S73-S78.

"Fosrenol"—Retreived from the Internet at URL:http://web.archiveorg/web/20050901114025/www.fosrenol.com/presribinginfo.pdf. Sep. 11, 2005.

Chiang, S-S., et al., "Lanthanum Carbonate (Fosrenolâ) Efficacy and Tolerability in the Treatment of Hyperphosphatemic Patients with End Stage Renal Disease," Clinical Nephrology, vol. 63, No. 6, Jun. 2005, p. 461-470.

Cullel-Young, M., et al., "Lanthanum Carbonate—Treatment of Hyperphosphatemia," Drugs of the Future, vol. 28, No. 3, Mar. 1, 2003, pp. 224-228.

Properties of CAB-O-SIL® M-5P Fumed Silica, 2004 Cabot Corporation, pp. 1-6.

Influence of CAB-O-SIL® M-5P on the Angle of the Repose and Flow Rates of Pharmaceutical Powders, Sep. 2004 Cabot Corporation, pp. 1-10.

Applications of CAB-O-SIL® M-5P Fumed Silica in the Formulation and Design of Solid Dosage Forms, 2004 Cabot Corporation, pp. 1-5.

Hutchison AJ Calcitriol, lanthanum carbonate, and other new phosphate binders in the management of renal osteodystrophy. Perit Dial Int. 1999, 19 Suppl 2, S408-S412.

Patent Abstract of Japan abstracting Publication No. 62-145024 Jun. 29, 1987.

"The Principal and Technique of Formulations," Korean book, partial English translation, www.shinilbooks.com.

Supplementary Partial European Search Report for EP 04 76 1727 completed Sep. 5, 2006.

Korean Office Action dated Oct. 11, 2007 issued for corresponding Korean Patent Application No. 10-2006-7003792. (4 pgs).

\* cited by examiner

XRPD of Hydrated Lanthanum Carbonate

XRPD of Excipient Starting Materials and Anhydrous Lanthanum Carbonate

Stress Study of Hydrated Lanthanum Carbonate 60 C/95% RH

Stress Study of Hydrated Lanthanum Carbonate 60 C/65% RH

Stress Study of Hydrated Lanthanum Carbonate/D-Mannitol 60 C/65% RH

Stress Study of Hydrated Lanthanum Carbonate/D-Sorbitol 60 C/65% RH

Stress Study of Hydrated Lanthanum Carbonate/Dextrates, 60 C/65% RH

Stress Study of Hydrated Lanthanum Carbonate/β-Cyclodextrin, 60 C/95% RH

Stress Study of Hydrated Lanthanum Carbonate/Corn Starch, 60 C/95% RH

Stress Study of Hydrated Lanthanum Carbonate/Anhydrous Lactose, 60 C/95% RH

Stress Study of Hydrated Lanthanum Carbonate/Lactose Monohydrate, 60 C/95% RH

Stress Study of Hydrated Lanthanum Carbonate/Microcrystalline Cellulose, 60 C/95% RH Stress Study of Hydrated Lanthanum Carbonate/D-Mannitol (96:4), 60 C/95% RH Decarboxylation rates of lanthanum carbonate to lanthanum hydroxycarbonate (HC)

US 7,381,428 B2

STABILIZED LANTHANUM CARBONATE COMPOSITIONS

This application is a continuation in part (CIP) of U.S. application Ser. No. 10/926,330 entitled "Pharmaceutical Formulation Comprising Lanthanum Compounds" filed Aug. 26, 2004 and published as U.S. publication No. 2005/0079135 on Apr. 14, 2005 which claims priority to U.S. Provisional application No. 60/497,560, filed Aug. 26, 2003 and U.S. Provisional application No. 60/517,078 filed Nov. 5, 2003. U.S. application Ser. No. 10/926,330, Provisional application No. 60/497,560, and Provisional application No. 60/517,078 are each incorporated by reference herein.

1. FIELD OF THE INVENTION

This invention relates to stabilized lanthanum carbonate compositions comprising a monosaccharide or disaccharide stabilizing agent, and to the treatment of subjects having hyperphosphatemia by administering a pharmaceutical composition containing a therapeutically effective amount of a stabilized lanthanum carbonate composition.

2. BACKGROUND OF THE INVENTION

Hyperphosphatemia is a particular problem of patients with chronic renal insufficiency or chronic kidney disease (CKD). Approximately 70% of patients with end stage renal disease (ESRD) on renal dialysis therapy require treatment for hyperphosphatemia. This condition can lead to severe bone problems and metastatic calcification of skin and major organs and is associated with significant morbidity and mortality. Conventional dialysis fails to reduce the levels of phosphate in the blood, so that levels rise in time. Elevated phosphate levels are treated using a combination of dietary restrictions and phosphate-binding agents.

Another problem of patients with chronic renal insufficiency is secondary hyperparathyroidism. It is also important in patients with chronic renal insufficiency to avoid and treat secondary hyperparathyroidism.

Certain forms of lanthanum carbonate have been used to treat hyperphosphatemia in patients with renal failure (see, e.g., JP 1876384).

U.S. Pat. No. 5,968,976, owned by the assignee of the present invention, describes the preparation and use in a pharmaceutical composition of certain hydrates of lanthanum carbonate for the treatment of hyperphosphatemia.

However, lanthanum carbonate has a tendency to degrade to lanthanum hydroxycarbonate. This process is accelerated by moisture and heat. There is a need in the art to prevent this degradation because current regulatory requirements preclude detectable decarboxylation for administration to patients. The present invention is based on the surprising finding that monosaccharides or disaccharides significantly retard the degradation of lanthanum carbonate, whereas more complex saccharides (e.g., corn starch and β-cyclodextrins) do not. Stabilized compositions of lanthanum carbonate can be used in pharmaceutical preparations and for treating subjects having hyperphosphatemia.

3. SUMMARY OF THE INVENTION

In accordance with the present invention, a stabilized lanthanum carbonate composition is provided, comprising a pharmaceutically effective amount of lanthanum carbonate having the general formula $La_2(CO_3)_3 \cdot xH_2O$ wherein x has a value from 0 to 10, and at least one pharmaceutically acceptable monosaccharide or disaccharide, wherein the monosaccharide or disaccharide is present in an amount of at least about 1% by weight based on the total weight of the composition. As indicated hereinafter, the invention is applicable to the treatment of subjects susceptible to or suffering from hyperphosphatemia, at risk for chronic kidney disease (CKD), having stage one to five CKD, susceptible to or suffering from soft tissue calcification associated with CKD, susceptible to or suffering from secondary hyperparathyroidism, or susceptible to or suffering from other as yet undiscovered conditions requiring control of phosphate absorption. This invention is also applicable to the treatment of subjects described in U.S. application Ser. No. 11/272,563 entitled "Treatment of Chronic Kidney Disease (CKD) Subjects using Lanthanum Compounds" filed on the same day as the present application.

Lanthanum carbonate in the form of a chewable tablet which is one embodiment of the present invention (available as Fosrenol® from Shire Pharmaceuticals, Wayne, Pa.) has been approved by the FDA to treat hyperphosphatemia in ESRD subjects and it currently being marketed.

The above features and many other attendant advantages of the invention will be better understood by reference to the following detailed description.

4. BRIEF DESCRIPTION OF DRAWINGS

5. DETAILED DESCRIPTION OF THE INVENTION

5.1. General Definitions

Figure 1:
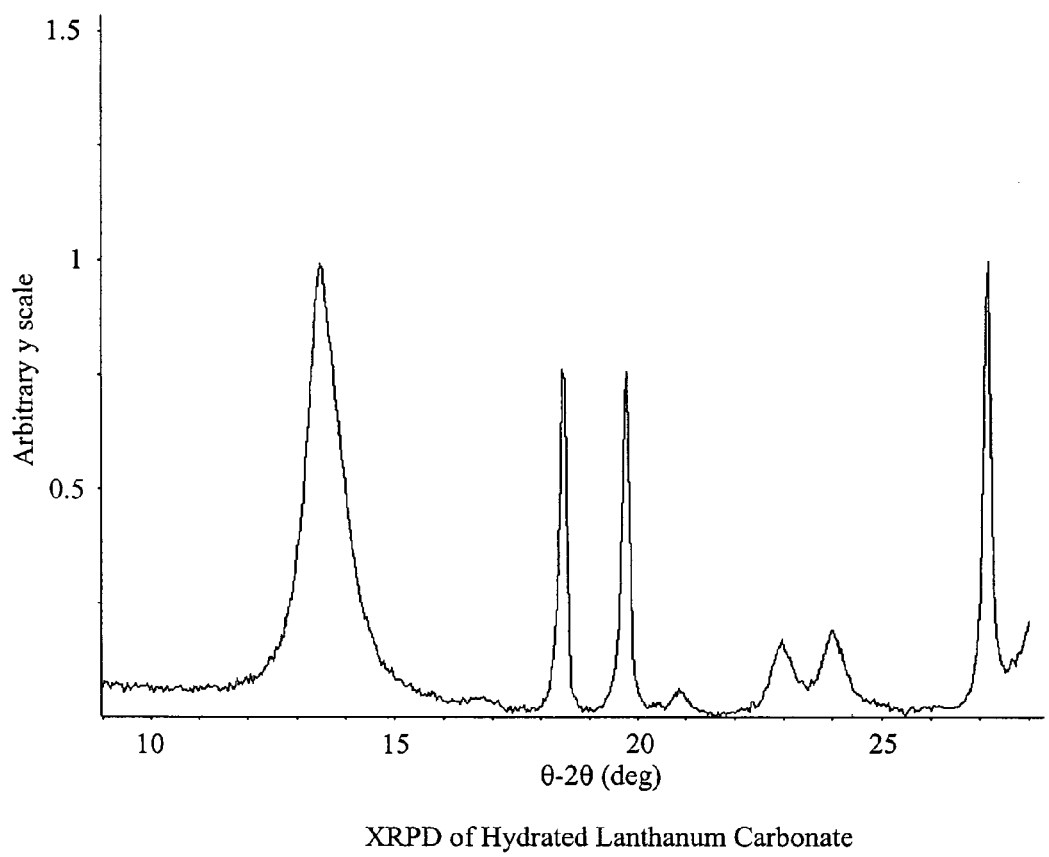
FIG. 1 is an XRPD (x-ray powder diffraction) pattern of substantially pure hydrated lanthanum carbonate having a water content approximately equivalent to 4-5 moles of water.

As used herein, the terms "treat," "treating," or "treatment" mean the prevention, reduction, amelioration, partial or complete alleviation, or cure of hyperphosphatemia, chronic kidney disease (CKD), severe bone problems, soft tissue calcification, secondary hyperparathyroidism, or other as yet undiscovered conditions requiring control of phosphate absorption.

Further, as used herein, the term "subject" refers to a mammal (e.g., any veterinary medicine patient such as a domesticated animal, such as a dog or cat), or a human patient.

The terms "about" or "approximately" mean within an acceptable range for the particular parameter specified as determined by one of ordinary skill in the art, which will depend in part on how the value is measured or determined, e.g., the limitations of the measurement system. For example, "about" can mean a range of up to 20% of a given value. Alternatively, particularly with respect to biological systems or processes, the term can mean within an order of magnitude, preferably within 5-fold, and more preferably within 2-fold, of a value.

The term "dextrates" as used herein refers to a purified mixture of saccharides that is mostly dextrose (e.g., not less than about 93.0% and not more than about 99.0%, calculated on the dried basis) and that results from a controlled enzymatic hydrolysis of starch. Dextrates can be either anhydrous or hydrated. "Dextrates" can refer to dextrates as defined its official monograph found in *National Formulary 21* (printed by Webcom Limited in Toronto, Canada; 2003). Dextrates are available from JRS Pharma (Patterson, N.Y.) as Emdex®.

As used herein, a "stabilized composition" or "stabilized lanthanum carbonate composition" refers to a composition containing lanthanum carbonate (of any hydration state including anhydrous lanthanum carbonate) and one or more monosaccharides or disaccharides. Preferably, the total amount of monosaccharides, disaccharides, or combination thereof is present in the stabilized composition in an amount of at least about 1% by weight. The lanthanum carbonate in a stabilized lanthanum carbonate composition degrades into lanthanum hydroxycarbonate at a slower rate compared to lanthanum carbonate alone or not in the presence of other materials. For example, after 7 days at 60° C. and 95% relative humidity, lanthanum carbonate in a lanthanum carbonate composition stabilized with at least about 4% monosaccharide, disaccharide, or combination thereof does not detectably (by present analytical techniques) degrade into lanthanum hydroxycarbonate. In contrast, under the same conditions, substantially pure lanthanum carbonate begins to decompose into lanthanum hydroxycarbonate after only 1 day.

A "pharmaceutically effective amount" or "therapeutically effective amount" as used herein is an amount or dose of lanthanum carbonate sufficient (i) to detectably decrease the serum phosphate levels of a subject or (ii) at a minimum, to keep the serum phosphate levels of a subject substantially constant.

"Lanthanum carbonate" as used herein encompasses all hydrated forms of lanthanum carbonate as well as anhydrous lanthanum carbonate.

"Percent" or "%" as used herein refers to the percentage by weight of the total composition.

The term "substantially pure lanthanum carbonate" refers to lanthanum carbonate of about 90% purity or greater, on an anhydrous basis.

The term "symptom(s)" of those at risk for or having hyperphosphatemia, CKD, soft tissue calcification associated with CKD, or secondary hyperparathyroidism may be any functional or structural abnormality experienced by a subject and indicating kidney dysfunction, e.g., those described in Section 5.6, infra. Among other abnormalities, as an example, one or more of the following symptoms may indicate risk for or the presence of CKD: a creatinine concentration of above about 1.6 mg/dL, a blood urea nitrogen (BUN) of above about 20 mg/dL, a blood phosphate level of above about 4.5 mg/dL, any detectable amount of blood in the urine, a urine protein concentration above about 100 mg/dL, a urine albumin concentration above about 100 mg/dL, an intact parathyroid hormone (PTH) concentration in the blood of above about 150 pg/mL, or a glomerular filtration rate (GFR) of below about 90 mL/min/1.73 m$^2$.

5.2. Lanthanum Carbonate

The stabilized compositions of the invention can contain lanthanum carbonate having the general formula $La_2(CO_3)_3 \cdot xH_2O$, wherein x has a value from 0 to 10. Preferably, x has a value from 3 to 8, desirably from 3 to 6. Most preferably, x may have an average value of about between 4 and 5. The hydration level of the lanthanum compound can be measured by methods well known in the art, such as thermo gravimetric analysis (TGA) or x-ray powder diffraction (XRPD).

Lanthanum carbonate has a tendency to degrade via decarboxylation to lanthanum hydroxycarbonate as shown:

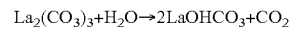

$$La_2(CO_3)_3 + H_2O \rightarrow 2LaOHCO_3 + CO_2$$

The hydroxycarbonate product results from electrophilic or nucleophilic attack on the carbonyl moiety of lanthanum carbonate. This process is accelerated in the presence of moisture or heat and appears to be self-catalyzing. Hence, even a very small amount of lanthanum hydroxycarbonate in lanthanum carbonate formulations causes rapid and excessive degradation. Furthermore, there is a need in the art to prevent this degradation since, as noted above, current regulatory requirements preclude detectable decarboxylation for administration to patients. As a result, formulations that eliminate or substantially retard degradation are highly preferred.

In accordance with the present invention, the presence of at least about 1% by weight of one or more monosaccharides or disaccharides in the lanthanum carbonate composition significantly retards the degradation of lanthanum carbonate. Surprisingly, the addition of such a stabilizing agent is effective to minimize degradation irrespective of the degree of hydration (if any) of the lanthanum carbonate. For example, while unformulated lanthanum carbonates degrade to lanthanum hydroxycarbonate within about 9-12 months at room temperature, in the presence of a mono- or disaccharide (about 70% by weight), substantially no detectable degradation occurs for up to or more than 3 years under standard ambient conditions.

Without being bound by any theory, the stabilizing effect of the monosaccharide and disaccharide stabilizing agents of this invention is believed to be attributed to the availability of reactive alcohol —OH groups on such materials; on the other hand, polysaccharides (wherein the alcohol groups are further reacted to link the monosaccharide units) do not exhibit such stabilizing characteristics. Water reacts preferentially with the available alcohol groups on the monosaccharides or disaccharides, leaving the carbonyl groups of the lanthanum carbonate intact so that the anti-hyperphosphatemic agent is not degraded.

The degradation of lanthanum carbonate into lanthanum hydroxycarbonate can be observed by examining an x-ray powder diffraction (XRPD) pattern of a potentially degraded lanthanum carbonate sample. The presence of observable peaks corresponding to lanthanum hydroxycarbonate in the sample pattern indicates degradation whereas the absence of observable peaks indicates no detectable degradation. Example 5 demonstrates the use of XRPD patterns to observe the degradation of lanthanum carbonate into lanthanum hydroxycarbonate.

Additional advantages of the instant invention include, but are not limited to, less expensive storage and handling costs due to a diminished need to refrigerate the stabilized lanthanum carbonate formulations. The stabilized formulations also provide enhanced product shelf-life resulting in less waste due to outdated product inventory.

Other advantages of the presently disclosed formulations can be found in the parent application (U.S. application Ser. No. 10/926,330) and include that formulating lanthanum carbonate with a mono- or disaccharide increases the palatability of the formulation and allows the formulation to be administered in chewable form without liquid.

5.3. The Monosaccharide and Disaccharide Stabilizing Agent

The stabilized compositions of the invention contain at least one monosaccharide or disaccharide. The monosaccharide, disaccharide, or mixture thereof is present in a total amount of at least about 1%, preferably from about 4% to about 90%, and more preferably from about 30% to about 70% by weight of the composition.

Suitable monosaccharides for use as stabilizing agents in the formulation of the present invention include, but are not limited to, glyceraldehyde, erythrose, threose, ribose, lyxose, xylose, arabinose, allose, talsoe, gulose, mannose, glucose (e.g., in the form of corn syrup), idose, galactose, altrose, dihydroxyacetone, erythrulose, ribulose, xyloketose, psicose, tagatose, sorbose, fructose, sorbitol, xylitol, inositol, erythritol, and mannitol in either the D- or L-configuration, including derivatives and analogs thereof. Monosaccharides for use in this inventions can be either cyclic (in either α- or β-form) or acyclic and can be used in the invention as mixtures. Other suitable monosaccharides include dextrose (D-glucose such as Cerelose® available from Fisher Scientific (Hampton, N.H.)).

Suitable disaccharides for use as stabilizers in the present invention include, but are not limited to, sucrose (for example, in the form of Di-Pac® available from Domino Foods in Baltimore, Md., Sugartab® available from JRS Pharma (Patterson, N.Y.), confectioner's sugar, or Nutab), lactose (including anhydrous lactose and lactose monohydrate), maltose, isomaltose, cellobiose, trehalose, maltitol (in the form of Lycasin® available from Roquette (Lestrem, France)), isomalt, lactitol, mixtures, dervatives, and analogs thereof. Disaccharides of this invention also include any combination of two monosaccharides linked by a glycosidic bond. Disaccharides can be either homodisaccharides (i.e., consisting of 2 monosaccharides that are the same) or heterodisaccharides (i.e., consisting of 2 monosaccharides that are different). Furthermore, monosaccharides and disaccharides can be used in the same formulation.

Other suitable monosaccharides and disaccharides can be found in *Remington: The Science and Practice of Pharmacy* ($20^{th}$ Edition, A. R. Gennaro editor, Lippincott Baltimore, Md.: Williams and Wilkins, 2000) at pages 409-413; and in *Biochemistry* ($2^{nd}$ Edition, Voet and Voet, New York: John Wiley & Sons, Inc., 1995) at pages 251-276. Hydrolyzed starches containing mono- and/or dissaccharides can also be used in the formulations of the invention.

Dextrates or sorbitol are preferably used as the monosaccharide or disaccharide stabilizing agent, in an amount preferably from about 4% to about 90% by weight of the formulation. In a preferred embodiment of the formulation of the invention, dextrates is incorporated as the stabilizing agent in an amount of about 70% by weight of the formulation. In another preferred embodiment of the formulation of the invention, sorbitol is incorporated as the stabilizing agent in an amount of about 30% by weight of the formulation.

5.4. Excipients

The stabilized formulations of the invention may further comprise at least one excipient. The excipients used in the formulation administered by the present invention should be suitable for oral administration to renally impaired subjects. The excipients may include diluents, binders, and lubricants/glidants. Other agents such as disintegrants, colors, and flavors/sweeteners can be added to the formulation.

Suitable diluents can be chosen from, for example, calcium sulfate dihydrate, oligosaccharide, isomaltooligosaccharide, erythritol, polydextrose, dextrins, starch, maltodextrin, calcium lactate trihydrate, microcrystalline cellulose (such as Avicel® available from GFS Chemicals (Powell, Ohio)), hydrolyzed cereal solids (such as Maltrons or Mor-Rex™), amylose, or glycine. Additional diluents can include the mono- and disaccharides stabilizing agents discussed, supra. One or more diluents can be present in a formulation. The total diluent amount can be from about 1% to about 90%, preferably from about 4% to about 90%, and most desirably from about 40% to about 80% by weight of the composition.

Useful lubricants can be chosen from, for example, magnesium stearate, talc, polyethylene glycol, silica, colloidal anhydrous silica, colloidal silicon dioxide, hydrogenated vegetable oil, glyceryl behenate or glyceryl monostearate. One or more lubricants can be present in a formulation. The total lubricant amount can be from about 0.1% to about 6.0%, preferably from about 0.1% to about 5.0%, and most desirably from about 0.1% to about 4.0% by weight of the composition.

Useful glidants can be chosen from, for example, silica, colloidal anhydrous silica, colloidal silicon dioxide, or talc. One or more glidants can be present in a formulation. The total glidant amount can be from about 0.1% to about 6.0%, preferably from about 0.1% to about 5.0%, and most desirably from about 0.1% to about 4.0% by weight of the composition.

It may also be advantageous to incorporate an antioxidant, for example, ascorbic acid, alpha tocopherol or butylated hydroxyanisole in the formulation to enhance its storage life. One or more antioxidants can be present in the formulation. The total antioxidant amount can be from about 0.0001% to 1.0%, preferably from about 0.001% to about 0.1%, and most desirably from about 0.005% to 0.05% by weight of the composition.

5.5. Additional Active Ingredients

5.5.1. A Combination Formulation Comprising Lanthanum Carbonate and Vitamin D Often, a subject suffering from hyperphosphatemia or the symptoms of CKD is also vitamin D deficient. Levels of 25-hydroxy vitamin $D_2$ are low at values less than about 16 ng/mL and replacement treatment aims for levels of greater than or equal to about 16 ng/mL. Levels of 1, 25-dihydroxy vitamin D2 are low at values less than about 22 pg/mL and replacement treatment aims for levels of greater than about 22 pg/mL. Thus, it becomes desirable to produce and administer to a patient a formulation containing lanthanum carbonate and vitamin D or an analog of vitamin D.

Examples of vitamin D sources which may be used in a formulation of this invention include 1,25 dihydroxy-vitamin D, the active metabolite of vitamin D (calcitriol, rocalcitrol). Examples of suitable vitamin D analogs include doxercalciferol (Hectorol®, available from Bone Care International, Middleton, Wis.) and paricalcitol (Zemplar®, available from Abbott Laboratories, Abbott Park, Ill.). One or more vitamin D sources or vitamin D analogs can be present in a formulation.

Vitamin D can also be administered in a separate dosage form, but concurrently with the dosage form of this invention. In a specific embodiment, 100 USP units of vitamin D is administered once per day and 250 mg of the stabilized lanthanum carbonate formulation is administered three times per day to a patient requiring treatment.

5.5.2. A Combination Formulation Comprising Lanthanum Carbonate and a Calcium Source Hyperphosphatemic subjects or subjects having symptoms of CKD often suffer from hypocalcaemia (i.e., a blood calcium concentration below about 8.5 mg/dL). Hence, a formulation of the invention can include lanthanum carbonate and a calcium source.

Examples of forms of calcium include calcium carbonate (e.g., Tums® available from GlaxoSmithKline, Uxbridge, UK), calcium acetate (e.g., PhosLo® available from Nabi Biopharmaceuticals, Boca Raton, Fla.), and $CaCl_2$. One or more calcium sources can be present in a formulation.

A calcium source can also be administered in a separate dosage form, but concurrently with the dosage form of this invention. In a specific embodiment, 1-2 tablets containing 200 mg as calcium and 250 mg of the stabilized lanthanum carbonate formulation are each given 3 times per day to a patient requiring treatment.

5.5.3. A Combination Formulation Comprising Lanthanum and Vitamin K

A subject suffering from hyperphosphatemia or the symptoms of CKD can be vitamin K deficient. In another embodiment of the present invention, the formulation of the invention, in combination with vitamin K, is administered to a subject suffering from hyperphosphatemia or the symptoms of CKD to alleviate vitamin K deficiency.

Examples of vitamin K sources include vitamin K1 (phylloquinone), vitamin K2 (menaquinone), and vitamin K3 (menadione).

Vitamin K can be combined in the same formulation as the lanthanum formulation or can be given in a different formulation. In a specific embodiment, 2.5 to 25 mg of vitamin K1 are administered once per day and a lanthanum formulation is administered three times per day to a subject requiring treatment.

5.6. Subjects Treated with Stabilized Lanthanum Carbonate Formulations

Subjects susceptible to or suffering from hyperphosphatemia, at risk for chronic kidney disease (CKD), having stage one to five CKD, susceptible to or suffering from soft tissue calcification associated with CKD, susceptible to or suffering from secondary hyperparathyroidism, or susceptible to or suffering from other as yet undiscovered conditions requiring control of phosphate absorption, can be treated by administering a therapeutically effective amount of a stabilized lanthanum carbonate formulation of the present invention.

5.6.1. Chronic Kidney Disease (CKD)

The National Kidney Foundation-Kidney Disease Outcomes Quality Initiative ("NKF-K/DOQI" or "K/DOQI," as referred to herein) has defined chronic kidney disease (CKD) as either (1) having kidney damage as defined by structural or functional abnormalities of the kidney for 3 months or longer with or without a decreased glomerular filtration rate (GFR) or (2) having a GFR of less than 60 mL/min/1.73 $m^2$ for 3 months or longer with or without kidney damage. Structural or functional abnormalities are manifested by symptoms such as either pathologic abnormalities or markers of kidney damage, including abnormalities identified in imaging studies or the composition of blood or urine.

Examples of markers of kidney damage include a plasma creatinine concentration of above about 1.6 mg/dL and a blood urea nitrogen (BUN) concentration of above about 20 mg/dL. Typically, both of these markers are elevated in individuals with CKD. Additional markers of kidney damage can include hematuria (i.e., any detectable amount of blood in the urine), proteinuria (i.e., protein concentrations in urine above about 100 mg/dL), albuminuria (i.e., albumin concentrations in urine above about 100 mg/dL), an intact parathyroid hormone (PTH) concentration in the blood above about 150 pg/mL, or blood phosphate levels of above about 4.5 mg/dL. One specific marker of kidney disease is a GFR rate above normal (i.e., a GFR above about 90 mL/min/1.73 $m^2$), however a below normal GFR also indicates CKD.

K/DOQI has published guidelines that define five different stages of CKD (*Am J Kidney Dis.* 2001, 37(suppl 1):S1-S238). The following table provides a description of each of the five stages of CKD and the GFR ranges for each of the stages.

| Five Stages of Chronic Kidney Disease (CKD) | | |
|---|---|---|
| Stage | Description | GFR (mL/min/1.73 m$^2$) 90-120 (with CKD symptoms) |
| | At risk | |
| 1 | Kidney damage with normal or elevated GFR | ≧90 |
| 2 | Kidney damage with mildly reduced GFR | 60-89 |
| 3 | Moderately reduced GFR | 30-59 |
| 4 | Severely reduced GFR | 15-29 |
| 5 | Kidney Failure (ESRD) | <15 (or dialysis) |

Hyperphosphatemia in CKD subjects has several secondary effects. When a subject suffers from hyperphosphatemia, excess serum phosphate precipitates serum calcium causing widespread ectopic extraskeletal calcification. Unwanted calcium deposits can occur in cardiovascular tissue, resulting in an increased risk of cardiovascular complications that often lead to death. Additionally, increased serum phosphate decreases intestinal calcium absorption. These two mechanisms work concurrently to reduce serum calcium levels.

A reduction in serum calcium levels can contribute to an increase in the production of parathyroid hormone (PTH) and to the development of secondary hyperparathyroidism. Furthermore, recent studies show that high phosphate levels can stimulate PTH production directly and lead to secondary hyperparathyroidism. Continual stimulation of PTH secretion induces hyperplasia of the parathyroid gland and may lead to a parathyroidectomy becoming necessary.

It is believed that the method of the present invention involving the administration or a stabilized lanthanum carbonate formulation not only reduces plasma phosphate levels but ameliorates the effects of CKD in subjects susceptible to or having any of stages one to five CKD, including hyperphosphatemia, ectopic extraskeletal calcification, serum hypocalcemia, and secondary hyperparathyroidism. It should however, be understood that this invention is not limited to any particular biochemical or physiological mechanism.

5.6.2. Methods of Treating Hyperphosphatemia

Subjects susceptible to or suffering from hyperphosphatemia can be treated by administering a therapeutically effective amount of a stabilized lanthanum carbonate formulation of the invention. Hyperphosphatemia as used herein refers to a condition of a patient having blood phosphate levels of above about 4.5 mg/dL.

5.6.3. Methods of Treating Chronic Kidney Disease (CKD)

A subject having a symptom or symptoms of chronic kidney disease (CKD) can be treated by administering to the subject a therapeutically effective amount of a stabilized lanthanum carbonate formulation of the present application. As indicated above, the subject treated may be at risk for CKD or have any of stages one to five CKD as defined above. Subjects at risk for CKD or who have any of stages one to five CKD who may be treated may have one or more of the following symptoms: a blood phosphate level of above about 4.5 mg/dL, a plasma creatinine concentration of above about 1.6 mg/dL, a BUN of above about 20 mg/dL, any detectable amount of blood in the urine, a urine protein concentration above about 100 mg/dL, a urine albumin concentration above about 100 mg/dL, an intact parathyroid hormone concentration in the blood above about 150 pg/mL, an abnormal GFR, or combination thereof.

The present method may be utilized to prevent the progression of renal pathology, e.g., by treating a subject displaying one or more symptoms of stage one CKD to prevent the development of CKD in the subject or by treating a subject having stage one CKD to prevent progression of the disease to stage two CKD, and so on.

5.6.4. Methods of Preventing Calcification

A subject having a symptom or symptoms of CKD can be treated for calcification of soft tissue associated with CKD by administering to the subject a therapeutically effective amount of a stabilized lanthanum carbonate formulation of the present invention.

Calcification can occur in any soft tissue. Soft tissue can include arterial tissue, cardiac muscle, heart valves, joints, skin and breast tissue.

5.6.5. Methods of Treating Secondary Hyperparathyroidism

A subject suffering from or having one or more symptoms of secondary hyperparathyroidism can be treated by administering to the subject a therapeutically effective amount of a stabilized lanthanum carbonate formulation of the present application.

Hyperparathyroidism is defined as a disease in a subject having an intact PTH level of about 150 pg/mL or greater. The symptoms of hyperparathyroidism include hypocalcaemia (i.e., a blood calcium level below about 8.5 mg/dL), hyperphosphatemia (i.e., a blood phosphate level of above about 4.5 mg/dL), and bone disorders (e.g., bone fractures or bone pain).

5.7. Administration of a Stabilized Lanthanum Carbonate Formulation

The lanthanum carbonate formulation can be orally administered to subjects in accordance with this invention in dosage forms varying from about 125 to about 2000 mg lanthanum carbonate as elemental lanthanum per meal. A typical dosage for an adult can be, e.g., 375 mg-6000 mg daily. More preferably, the dosage is 375-3750 mg/day. The dose can be divided and taken with each meal, for example a 250, 500, 750, or 1000 mg tablet, e.g., three times per day. Serum plasma levels can be monitored weekly and dosages can be modified until an optimal serum phosphate level is reached. Administration may be conducted in an uninterrupted regimen; such a regimen may be a long term regimen, e.g., a permanent regimen, for treating chronic conditions.

The lanthanum carbonate formulations can be orally administered, for example, in the form of tablets, capsules, chewable formulations, or the like. Frequently, due to their renal problems, subjects with hyperphosphatemia need to limit their liquid intake. Therefore, a lanthanum carbonate formulation that can be taken with no or limited amounts of liquid is desirable. For example, a lanthanum carbonate formulation, in the form of, e.g., beads, chewed or crushed tablets, powder, or sieved granules, may be sprinkled on food.

The lanthanum carbonate formulation is administered such that plasma levels of lanthanum are low, e.g., at least as low as those provided by a mean concentration curve where $C_{max}$, $T_{max}$, and AUC are preferably less than 1.5 ng/ml, about 12 hours, and less than 50 ng·hr/ml, respectively, for a dose of 3 g per day (e.g., 1 g three times per day). Preferably, the $C_{max}$ and AUC are less than 1.1 ng/ml and less than 32 ng·hr/ml, and desirably, $C_{max}$ and AUC are less than 0.5 ng/ml and less than 20 ng·hr/ml, for such dosage. $T_{max}$ values are essentially unaffected by dose and $C_{max}$ and AUC values vary linearly with dosage for oral dosages up to about 1500 mg/day. $C_{max}$ and AUC values plateau for dosages above about 1500 mg/day. All of these parameters have their common meanings.

It will be understood that the type of lanthanum carbonate formulation and the duration of the treatment will vary depending on the requirements for treatment of individual subjects. The precise dosage regimen will be determined by the attending physician or veterinarian who will, inter alia, consider factors such as body weight, age and specific symptoms. The physician or veterinarian may titrate the dosage of lanthanum carbonate administered to a subject to determine the correct dosage for treatment. For example, a physician can measure phosphate levels in a patient, prescribe a particular lanthanum carbonate dosage to the patient for a week, and evaluate after the week if the dosage is appropriate by remeasuring phosphate levels in the patient.

6. EXAMPLES

For the purposes of the Examples, the term "hydrated lanthanum carbonate" refers to lanthanum carbonate having a water content approximately equivalent to 4-5 moles of water.

The following tablets were prepared as generally described above:

TABLE 1A

| Ingredient | 250 mg tablet | 500 mg tablet | Function |
|---|---|---|---|
| Active Ingredient: | | | |
| Hydrated lanthanum (III) carbonate | 477.0 mg | 954.0 mg | Active |
| Other Ingredients: | | | |
| Dextrates | 1247.0 mg | 2494.0 mg | Stabilizes lanthanum carbonate |
| Colloidal anhydrous silica | 36.0 mg | 72.0 mg | Improves blending and flow |
| Purified talc | 30.0 mg | 60.0 mg | Lubricant or glidant |
| Magnesium stearate | 10.0 mg | 20.0 mg | Lubricant |
| Total | 1800 mg | 3600 mg | |

Formulation A

TABLE 1B

Formulation B

| | 250 mg tablet | 500 mg tablet | 750 mg tablet | 1000 mg tablet |
|---|---|---|---|---|
| Tablet diameter | 13 mm | 18 mm | 20 mm | 22 mm |
| Formulation | | | | |
| Lanthanum carbonate as elemental lanthanum | 250 mg | 500 mg | 750 mg | 1000 mg |
| Hydrated lanthanum carbonate | 477 mg | 954 mg | 1431 mg | 1908 mg |
| Dextrates (hydrated) | 533.2 mg | 1066.4 mg | 1599.6 mg | 2132.8 mg |
| Colloidal silicon dioxide | 21.2 mg | 42.4 mg | 63.6 mg | 84.8 mg |
| Magnesium stearate | 10.6 mg | 21.2 mg | 31.8 mg | 42.4 mg |
| Total weight | 1042 mg | 2048 mg | 3126 mg | 4168 mg |

6.1. Example 1

Preparation of Stabilized Hydrated Lanthanum Carbonate Chewable Tablets (250 mg, 500 mg, 750 mg, and 1000 mg)

The manufacturing process involves sieving and blending the active ingredient with the excipients followed by direct compression. More specifically the steps are as follows:

a) Blend the lanthanum carbonate and the excipients (e.g., dextrates, colloidal silicon dioxide, talc (optional) and magnesium stearate).

b) Compress the blend using standard tooling to the target compression weight.

TABLE 1C

Formulation C

| Formulation Components | Percent by Weight in the Tablet |
|---|---|
| Hydrated lanthanum carbonate | 45.8% |
| Colloidal silicon dioxide (e.g., Aerosil ® 200 available from Degussa Corp. (Piscataway, NJ)) | 2.1% |
| Dextrates | 51.1% |
| Magnesium sterate | 1.0% |

6.2. Example 2

Stabilized Lanthanum Carbonate Chewable Tablet Formulation Containing Sorbitol Stabilizing Agent The following lanthanum carbonate chewable tablet formulation comprising sorbitol can be manufactured as described in Example 1.

| Formulation Components | Percent by Weight in the Tablet |
| --- | --- |
| Hydrated lanthanum carbonate | 63.6% |
| Glyceryl dibehenate | 3.0% |
| Colloidal silicon dioxide (e.g., Aerosil ® 200) | 2.0% |
| Sorbitol | 30.4% |
| Talc | 1.0% |

6.3. Example 3

Stabilized Lanthanum Carbonate Chewable Tablet Formulation Containing Mannitol Stabilizing Agent The following lanthanum carbonate chewable tablet formulation comprising mannitol can be manufactured as described in Example 1.

| Formulation Components | Percent by Weight in the Tablet |
| --- | --- |
| Hydrated lanthanum carbonate | 63.6% |
| Glyceryl dibehenate | 3.0% |
| Colloidal silicon dioxide (e.g., Aerosil ® 200) | 2.0% |
| Mannitol | 30.4% |
| Talc | 1.0% |

6.4. Example 4

Stabilized Lanthanum Carbonate Chewable Tablet Formulation Containing Xylitol Stabilizing Agent The following lanthanum carbonate chewable tablet formulation comprising xylitol can be manufactured as described in Example 1.

| Formulation Components | Percent by Weight in the Tablet |
| --- | --- |
| Hydrated lanthanum carbonate | 63.6% |
| Glyceryl dibehenate | 3.0% |
| Colloidal silicon dioxide (e.g., Aerosil ® 200) | 2.0% |
| Xylitol | 30.4% |
| Talc | 1.0% |

6.5. Example 5

The Stabilization of Lanthanum Carbonate Formulations with Monosaccharide and Disaccharide Stabilizing Agents Excipient compatibility studies of hydrated lanthanum carbonate having a water content approximately equivalent to 4-5 moles of water and anhydrous lanthanum carbonate were performed to determine whether different classes of saccharide excipients would retard or prevent the appearance of decarboxylation products in thermally- and moisture-stressed solid lanthanum carbonate mixtures.

Conditions which would cause the formation of decarboxylation products in substantially pure hydrated lanthanum carbonate within one week were used. Mixtures of 1:1 or 96:4 (by weight) of hydrated lanthanum carbonate and a test excipient or 1:1 (by weight) anhydrous lanthanum carbonate and a test excipient were prepared and stressed, and samples were analyzed by XRPD (X-ray powder diffraction) as a function of exposure time.

6.5.1. Materials and Methods

6.5.1.1 Samples and Reagents

Substantially pure hydrated lanthanum carbonate and anhydrous lanthanum carbonate samples were utilized for this study. Test excipients (D-mannitol, D-sorbitol, dextrates, f-cyclodextrin, corn starch, anhydrous lactose, lactose monohydrate, and microcrystalline cellulose) were purchased from commercial suppliers and used as received.

6.5.1.2 Mixture Preparation

Weighed samples of hydrated lanthanum carbonate/excipient (1:1 or 96:4 by weight) or anhydrous lanthanum carbonate/excipient (1:1 by weight) were sealed into scintillation vials and placed onto a Turbula mixer. Samples were mixed for ten minutes to ensure sample homogeneity.

6.5.1.3 Humidity Chamber Preparation

Saturated salt solutions of $Na_2SO_4.10H_2O$ (~95% RH (relative humidity)) or $NaNO_3$ (65% RH) were prepared and placed into sealed chambers. The chambers were placed into a 60° C. oven overnight and the presence of solids was confirmed after 24 hours. These chambers were then subsequently used for the stressing studies of the various excipient/lanthanum carbonate mixtures. The lower humidity conditions were utilized for the D-sorbitol and dextrates excipients because they deliquesce under the more extreme conditions of 60° C./95% RH.

6.5.1.4 X-Ray Powder Diffractometer (XRPD)

XRPD analyses were performed using a Shimadzu XRD-6000 X-ray powder diffractometer using Cu Kα radiation. Samples were prepared for analysis by placing them in an aluminum holder with a silicon insert.

6.5.2. Results and Discussion

6.5.2.1 Characterization of Test Materials

Figure 2:
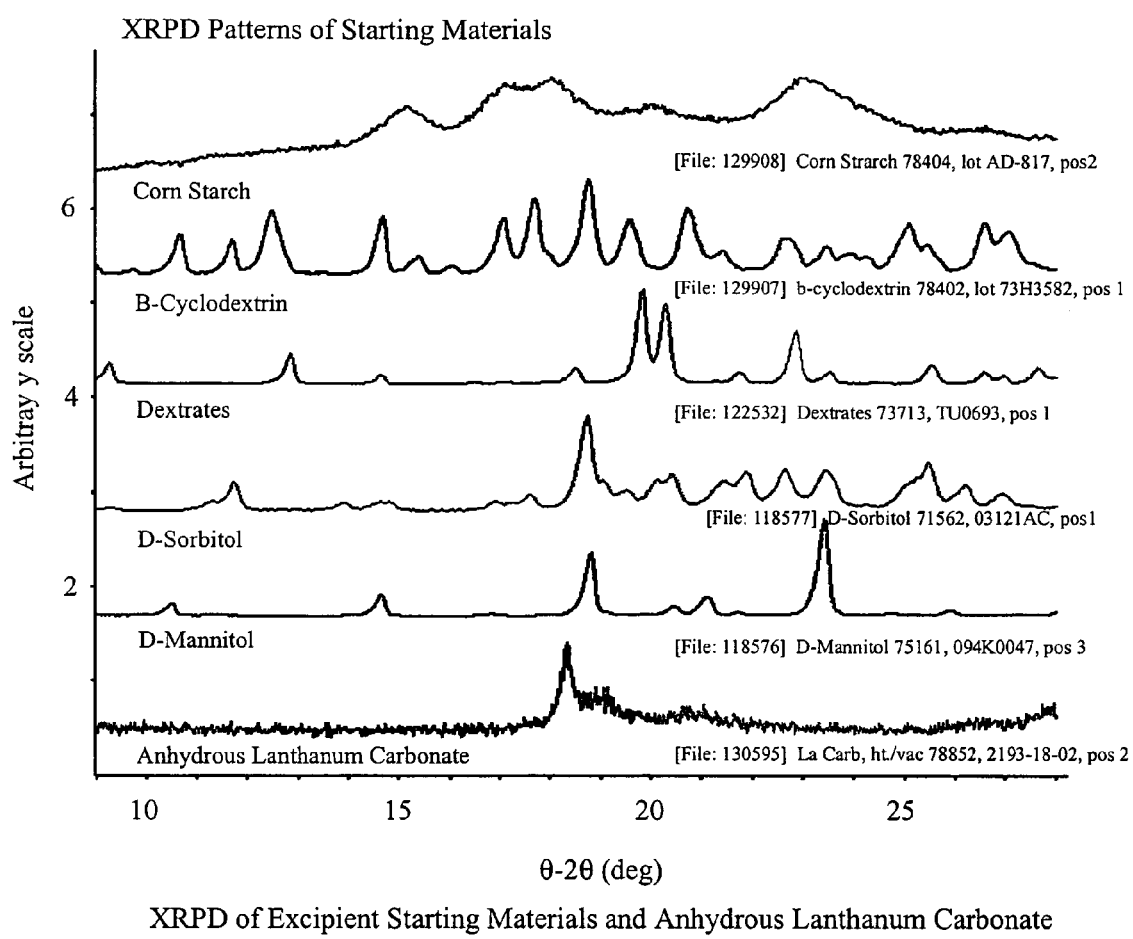
FIG. 2 illustrates XRPD patterns of substantially pure corn starch, β-cyclodextrin, dextrates, D-sorbitol, D-mannitol, and anhydrous lanthanum carbonate.

The unstressed, substantially pure hydrated lanthanum carbonate was crystalline by XRPD (FIG. 1). Excipients and anhydrous lanthanum carbonate used in this study were characterized by XRPD for specificity purposes, and their patterns are displayed in FIG. 2. All excipients exhibit sufficient specificity to allow the monitoring of lanthanum hydroxycarbonate (HC) formation.

6.5.2.2 Stress Studies of Hydrated Lanthanum Carbonate

At the experimental onset, the hydrated lanthanum carbonate was stressed under two conditions, 60° C./95% RH and 60° C./65% RH, in order to establish a baseline for monitoring decarboxylation. Individual samples were pulled after 1, 2, 3, 4, and 7 days and immediately analyzed by XRPD. In addition, pulls were made at 14 and 21 days under the 60° C./65% RH condition.

Figure 3:
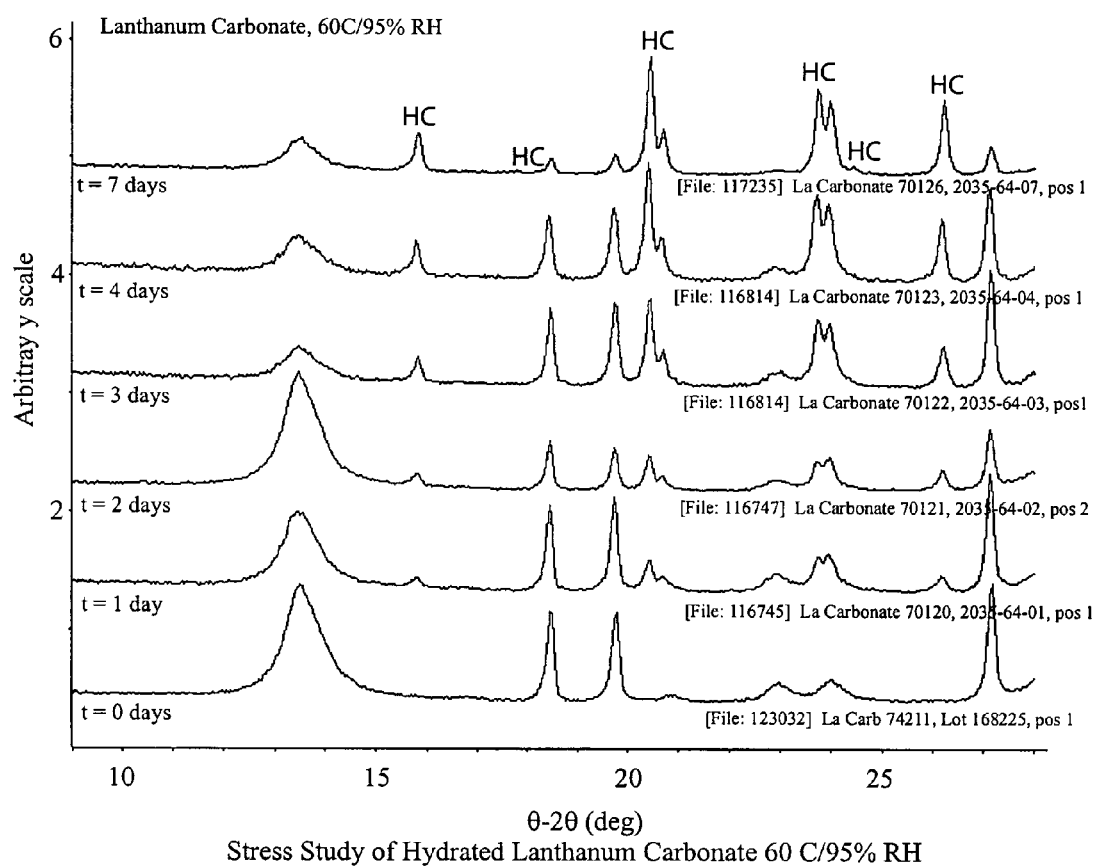
FIG. 3 illustrates XRPD patterns of hydrated lanthanum carbonate at 60° C./95% RH (relative humidity) for 0, 1, 2, 3, 4, and 7 days.
Figure 4:
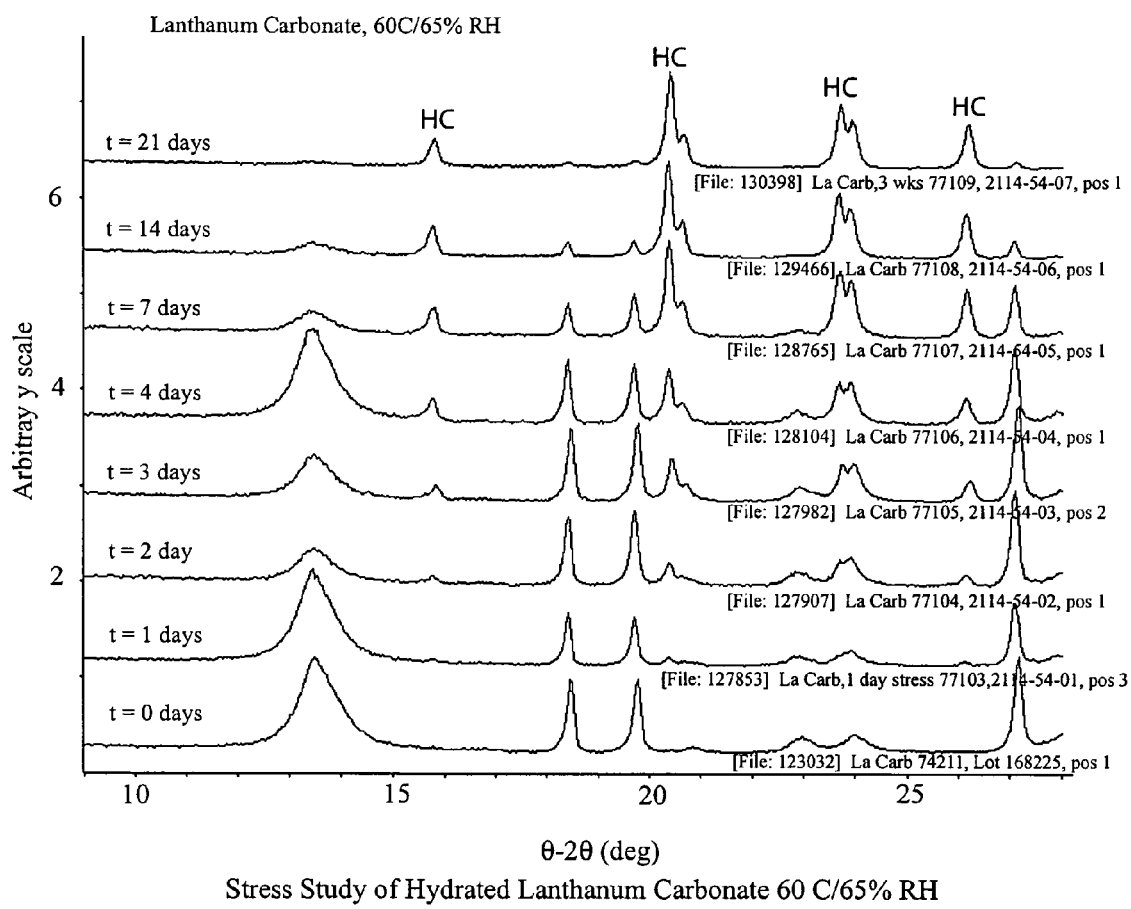
FIG. 4 illustrates XRPD patterns of hydrated lanthanum carbonate at 60° C./65% RH for 0, 1, 2, 3, 4, 7, 14, and 21 days.

FIG. 3 (60° C./95% RH conditions) and FIG. 4 (60° C./65% RH conditions) summarize the results. Under the 60° C./95% RH conditions, the decarboxylation product, HC, was initially seen after one day. When hydrated lanthanum carbonate was placed under 60° C./65% RH stress conditions, HC was again initially seen after a single day (FIG. 4).

6.5.2.3 Stress Studies of Hydrated Lanthanum Carbonate/D-Mannitol (60° C./65% RH Conditions)

Figure 5:
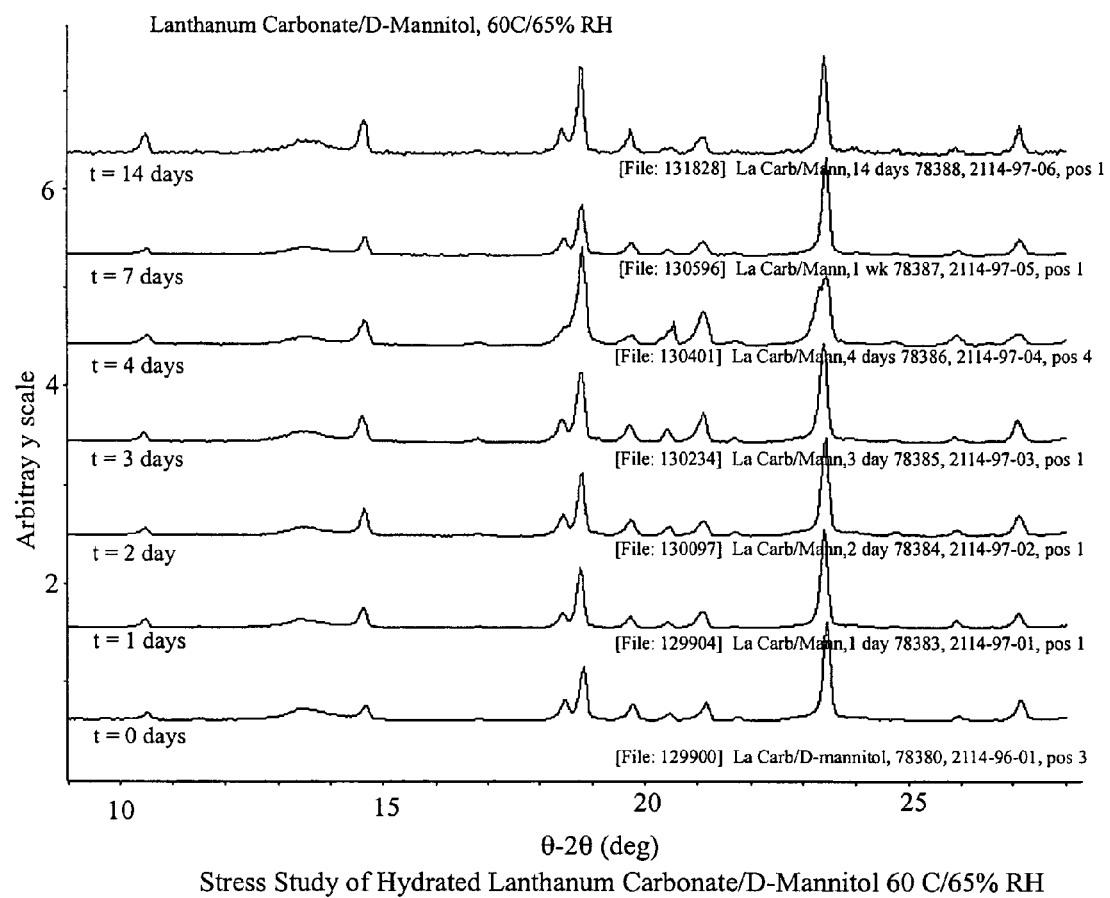
FIG. 5 illustrates XRPD patterns of a 1:1 (by weight) mixture of hydrated lanthanum carbonate/D-mannitol at 60° C./65% RH for 0, 1, 2, 3, 4, 7, and 14 days.

The 1:1 (by weight) mixtures of hydrated lanthanum carbonate/D-mannitol were stressed and analyzed over a two week period. The results are shown in FIG. 5. No decarboxylation of the hydrated lanthanum carbonate was seen over the entire length of the experiment.

6.5.2.4 Stress Studies of Hydrated Lanthanum Carbonate/D-Sorbitol (60° C./65% RH Conditions)

Figure 6:
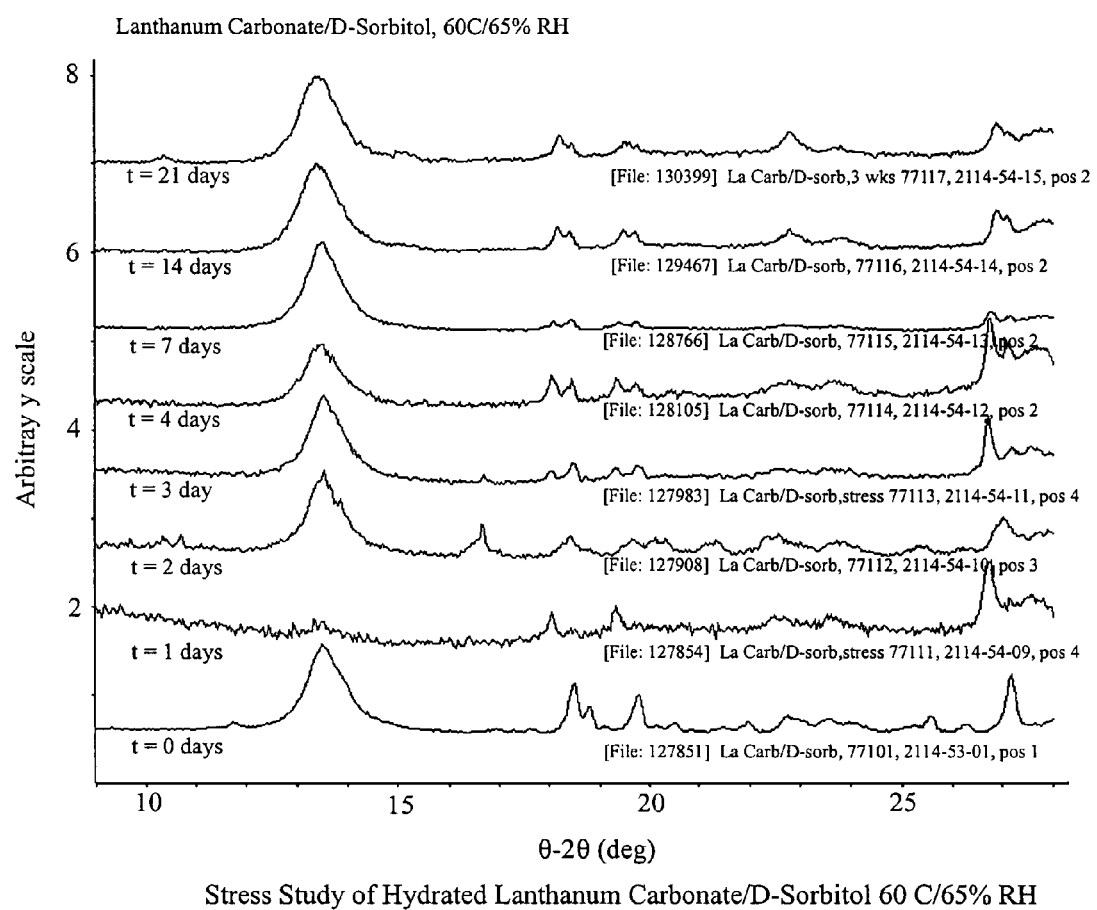
FIG. 6 illustrates XRPD patterns of a 1:1 (by weight) mixture of hydrated lanthanum carbonate/D-sorbitol at 60° C./65% RH for 0, 1, 2, 3, 4, 7, 14, and 21 days.

The 1:1 (by weight) mixtures of hydrated lanthanum carbonate/D-sorbitol were stressed over a three week period. Results are summarized in FIG. 6. No decarboxylation of the hydrated lanthanum carbonate was seen over the entire length of the experiment.

6.5.2.5 Stress Studies of Hydrated Lanthanum Carbonate/Dextrates (60° C./65% RH Conditions)

Figure 7:
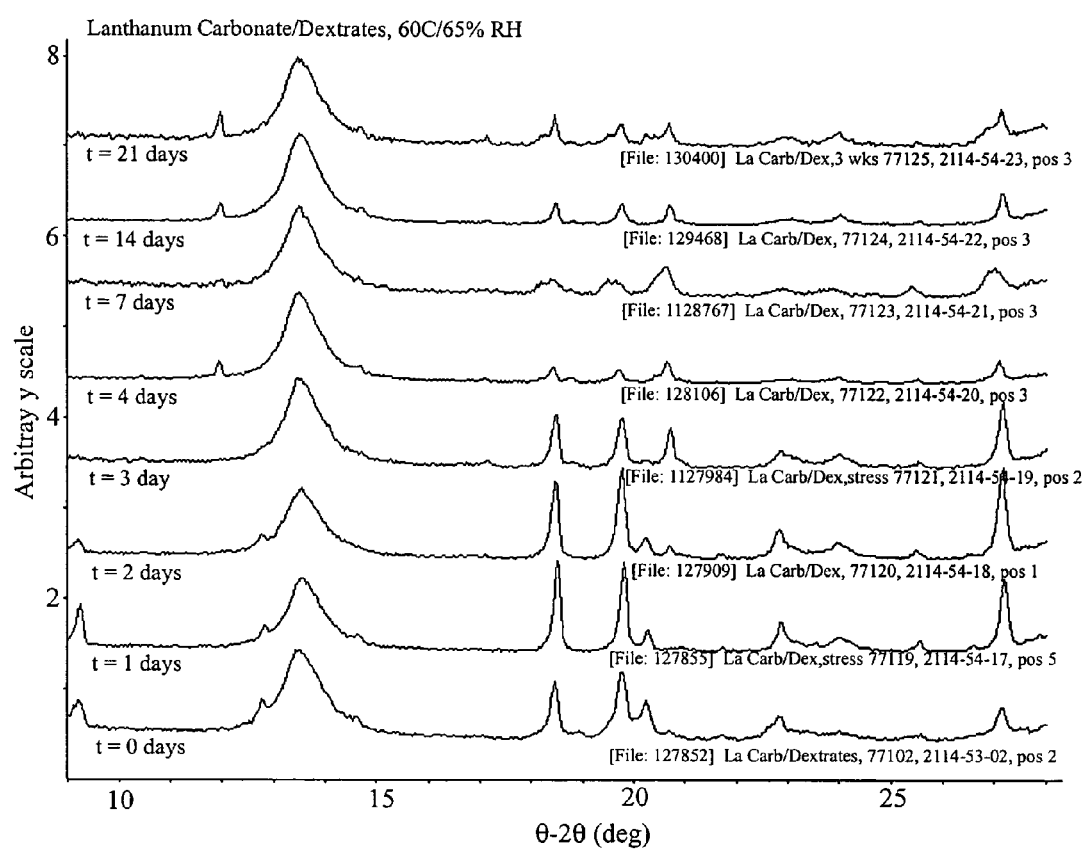
FIG. 7 illustrates XRPD patterns of a 1:1 (by weight) mixture of hydrated lanthanum carbonate/dextrates at 60° C./65% RH for 0, 1, 2, 3, 4, 7, 14, and 21 days.

The 1:1 mixtures (by weight) of hydrated lanthanum carbonate/dextrates were stressed over a three week period. Results are summarized in FIG. 7. No decarboxylation of the hydrated lanthanum carbonate was seen over the entire length of the experiment.

6.5.2.6 Stress Studies of Hydrated Lanthanum Carbonate/β-Cyclodextrin (60° C./95% RH Conditions)

Figure 8:
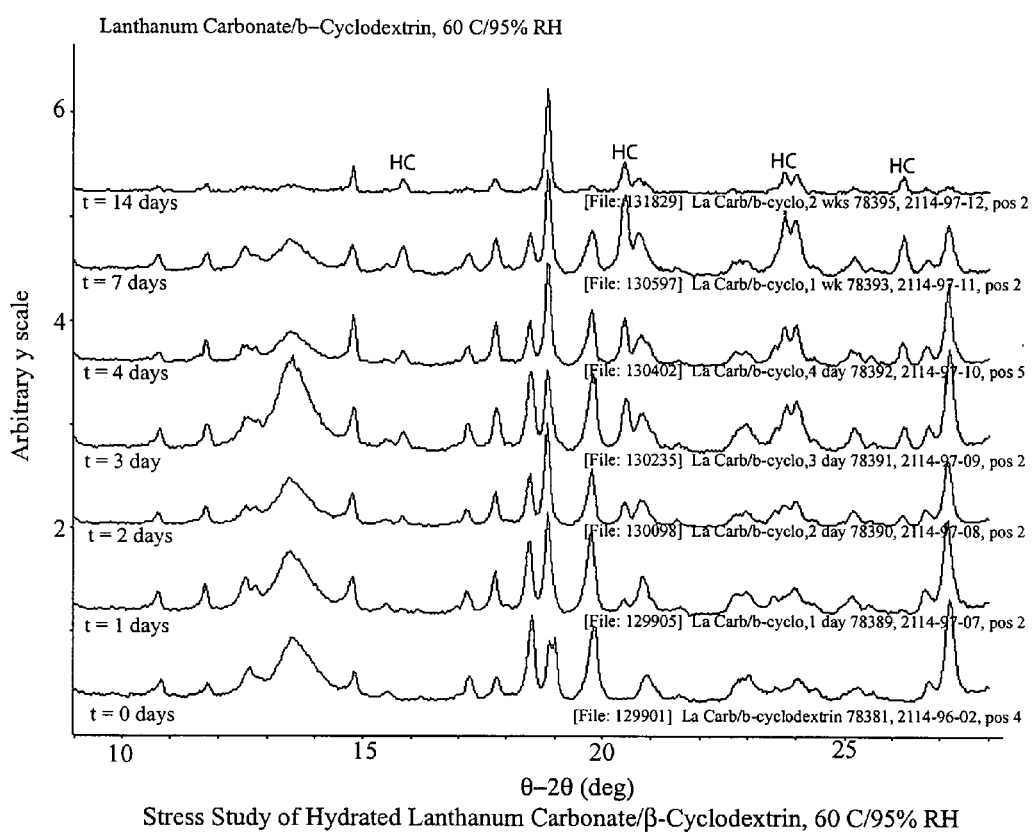
FIG. 8 illustrates XRPD patterns of a 1:1 (by weight) mixture of hydrated lanthanum carbonate/β-cyclodextrin at 60° C./95% RH for 0, 1, 2, 3, 4, 7, and 14 days.

The 1:1 (by weight) mixtures of hydrated lanthanum carbonate/O-cyclodextrin were stressed and analyzed over a two week period. The results are summarized in FIG. 8. The presence of the decarboxylation product HC was initially detected after 1 day of stressing.

6.5.2.7 Stress Studies of Hydrated Lanthanum Carbonate/Corn Starch (60° C./95% RH Conditions)

Figure 9:
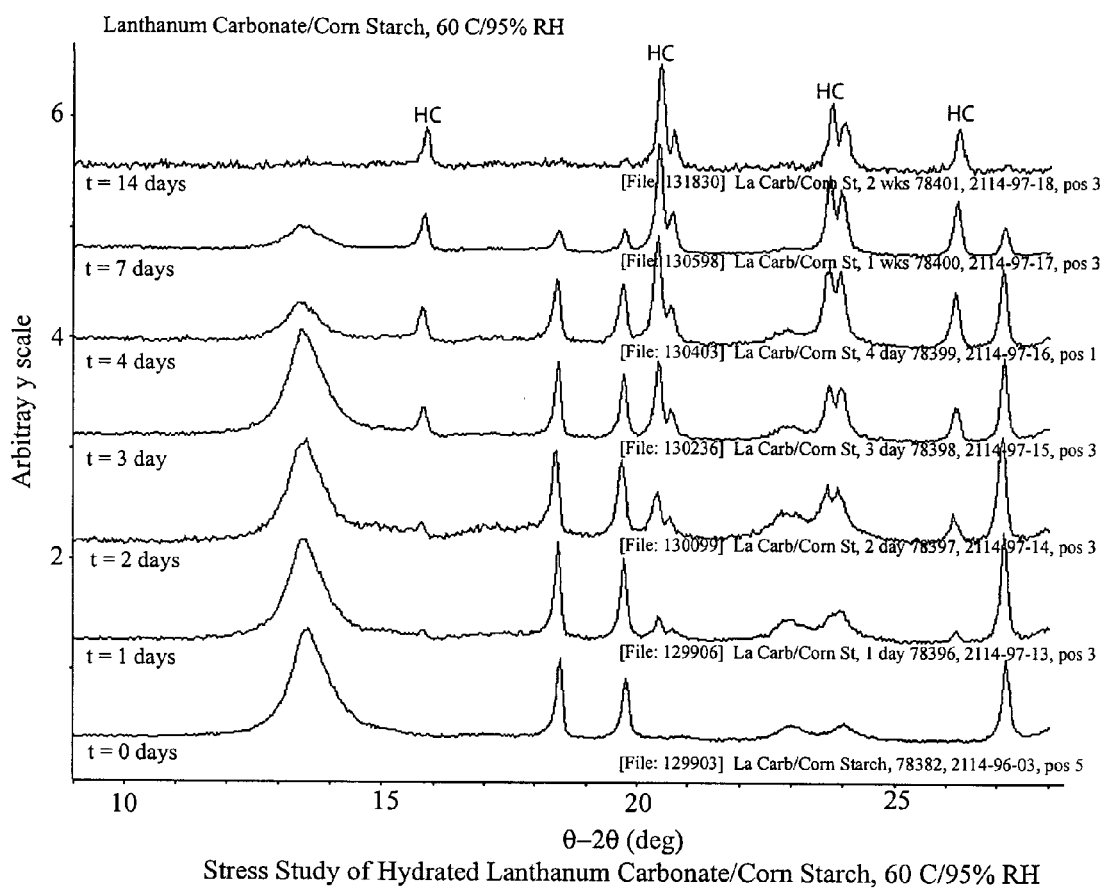
FIG. 9 illustrates XRPD patterns of a 1:1 (by weight) mixture of hydrated lanthanum carbonate/corn starch at 60° C./95% RH for 0, 1, 2, 3, 4, 7, and 14 days.

The 1:1 (by weight) mixtures of hydrated lanthanum carbonate/corn starch were set up for stressing over a two week period. The results are summarized in FIG. 9. The presence of the decarboxylation product HC was initially detected after 1 day of stressing.

6.5.2.8 Stress Studies of Anhydrous Lanthanum Carbonate/D-Mannitol (60° C./95% RH Conditions)

Figure 10:
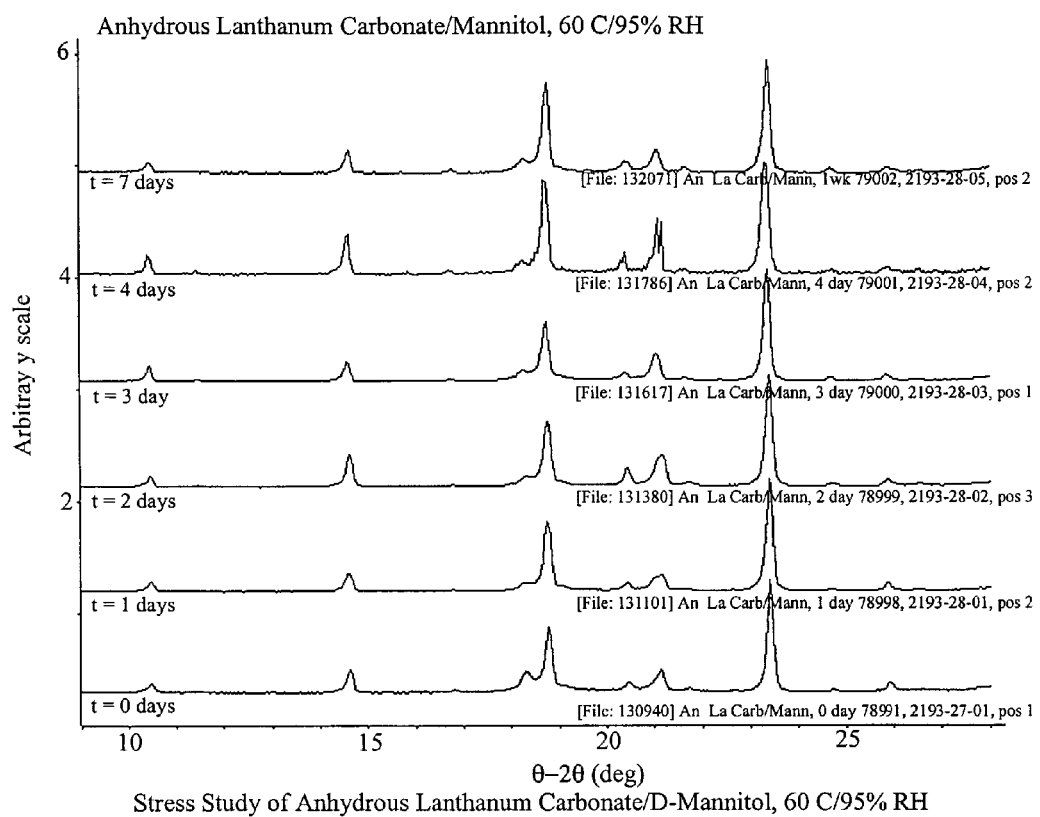
FIG. 10 illustrates XRPD patterns of a 1:1 (by weight) mixture of anhydrous lanthanum carbonate/D-mannitol at 60° C./95% RH for 0, 1, 2, 3, 4, and 7 days.

The 1:1 (by weight) mixtures of anhydrous lanthanum carbonate/D-mannitol were stressed and analyzed over a two week period. The results are summarized in FIG. 10. No decarboxylation of the anhydrous lanthanum carbonate was seen over the entire length of the experiment.

6.5.2.9 Stress Studies of Hydrated Lanthanum Carbonate/Anhydrous Lactose and Hydrated Lanthanum Carbonate/Lactose Monohydrate (60° C./95% RH Conditions)

Figure 11:
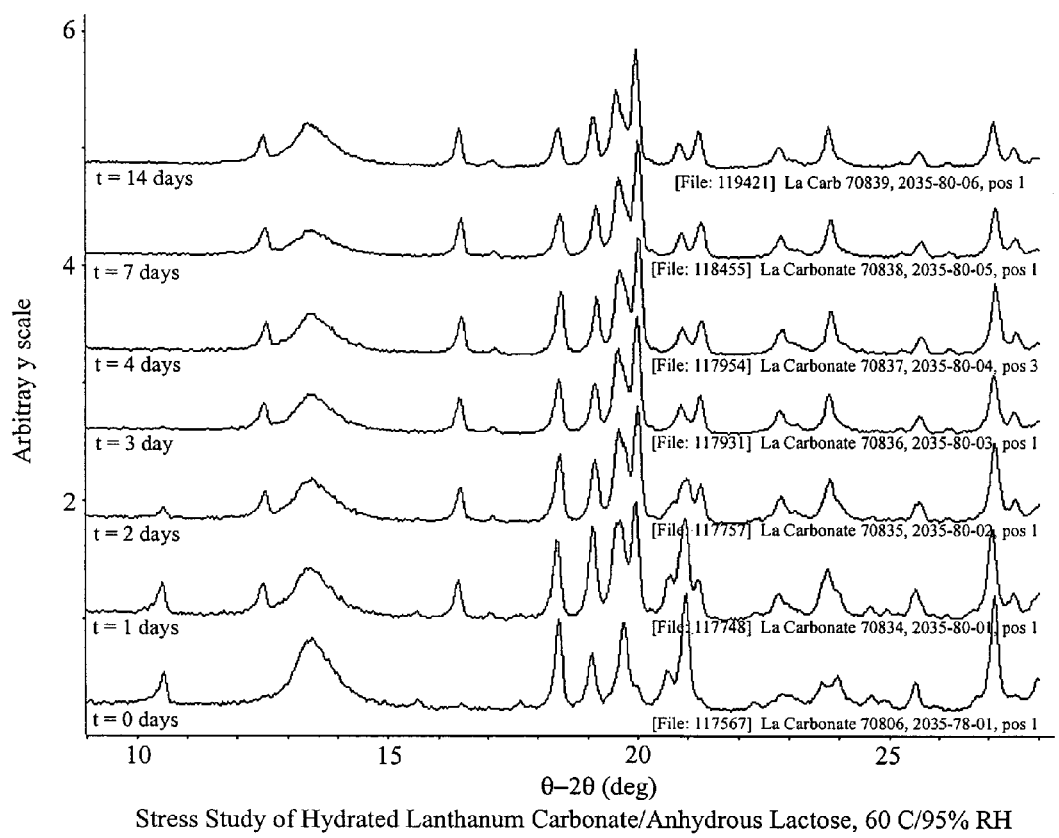
FIG. 11 illustrates the XRPD patterns of a 1:1 (by weight) mixture of hydrated lanthanum carbonate/anhydrous lactose at 60° C./95% RH for 0, 1, 2, 3, 4, 7, and 14 days.
Figure 12:
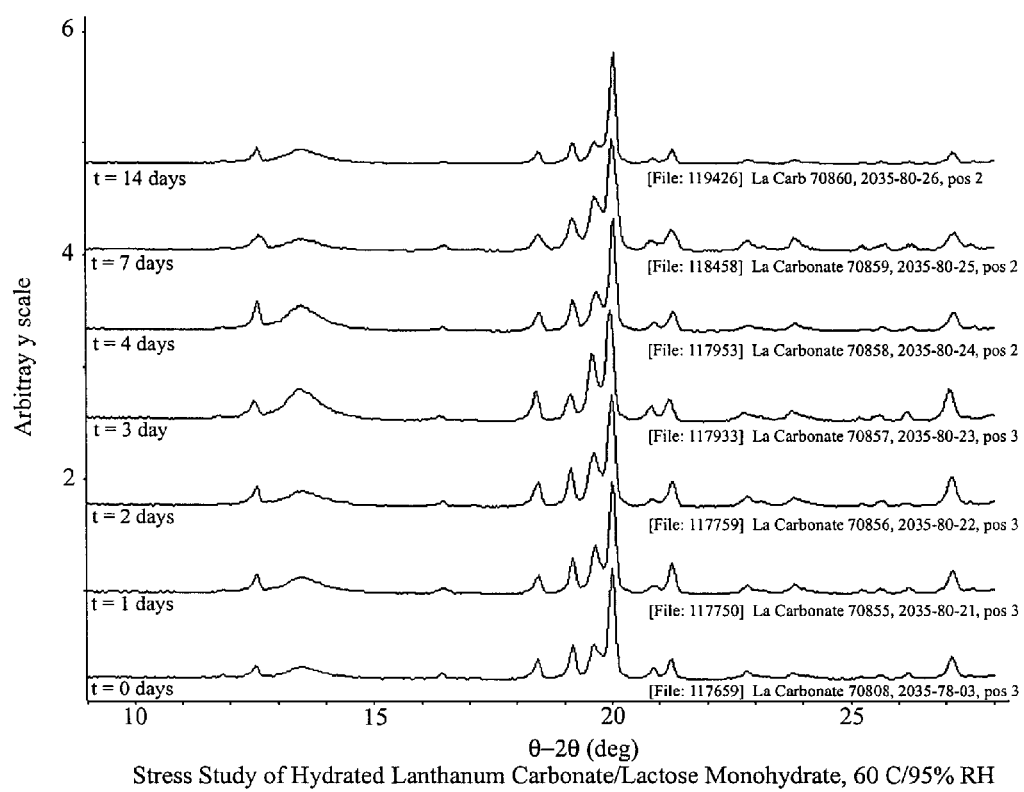
FIG. 12 illustrates the XRPD patterns of a 1:1 (by weight) mixture of hydrated lanthanum carbonate/lactose monohydrate at 60° C./95% RH for 0, 1, 2, 3, 4, 7, and 14 days.

1:1 (by weight) mixtures of hydrated lanthanum carbonate/anhydrous lactose and hydrated lanthanum carbonate/lactose monohydrate were stressed and analyzed over a two week period. The results are summarized in FIGS. 11 and 12 for hydrated lanthanum carbonate/anhydrous lactose and hydrate lanthanum carbonate/lactose monohydrate, respectively. No detectable decarboxylation of the hydrated lanthanum carbonate was observed in either mixture over the entire length of the experiment.

6.5.2.10 Stress Studies of Hydrated Lanthanum Carbonate/Microcrystalline Cellulose (60° C./95% RH Conditions)

Figure 13:
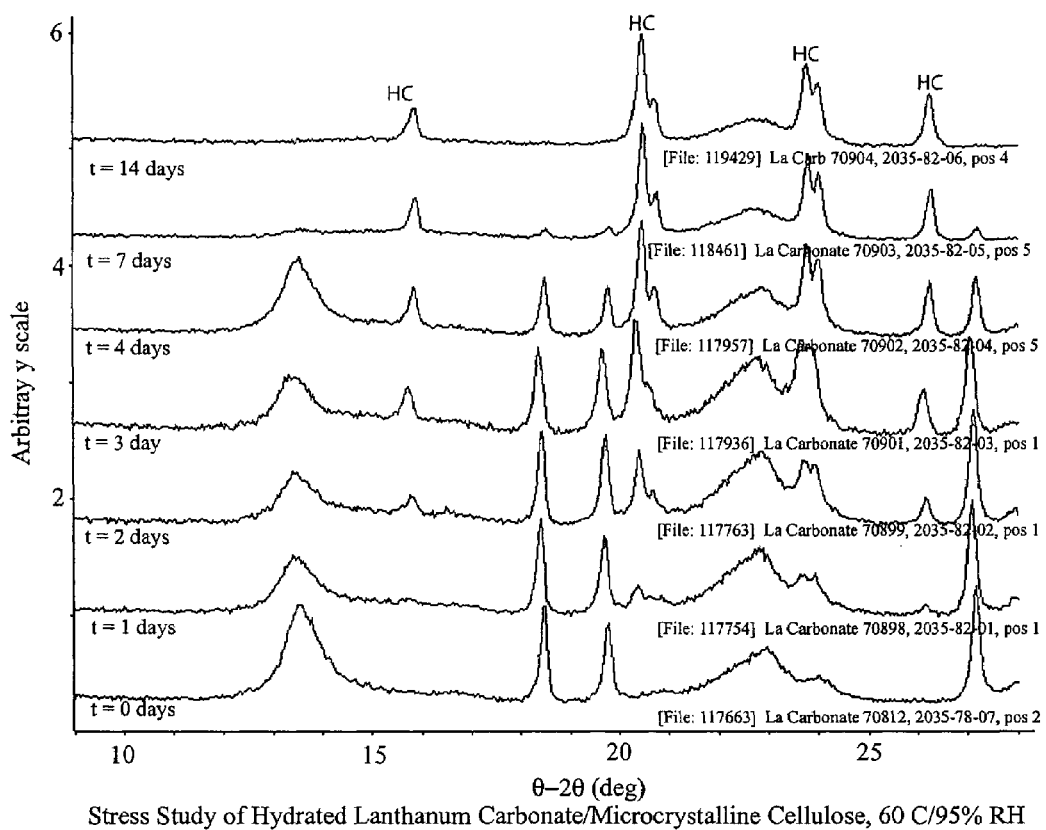
FIG. 13 illustrates the XRPD patterns of a 1:1 (by weight) mixture of hydrated lanthanum carbonate/microcrystalline cellulose at 60° C./95% RH for 0, 1, 2, 3, 4, 7, and 14 days.

The 1:1 (by weight) mixture of hydrated lanthanum carbonate/microcrystalline cellulose showed evidence of the decarboxylation of hydrated lanthanum carbonate after a single day of stressing at 60° C. and 95% relative humidity. The results are summarized in FIG. 13.

Figure 14:
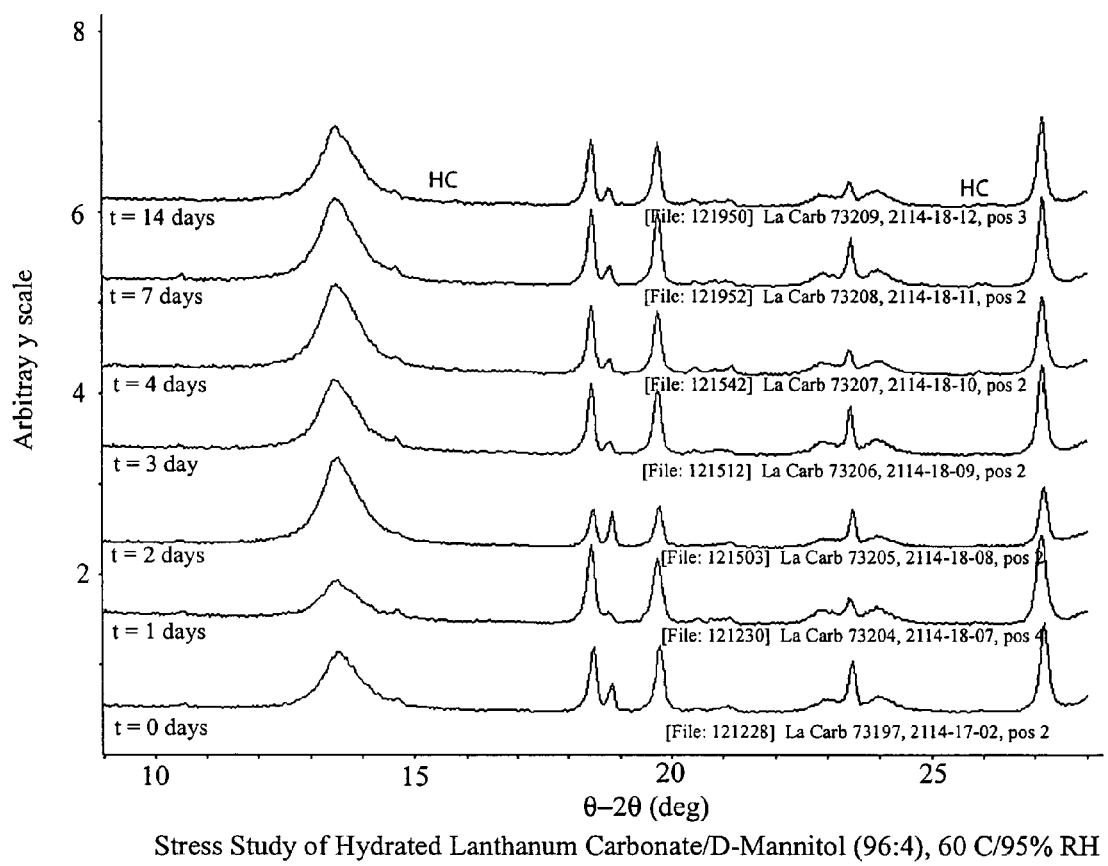
FIG. 14 illustrates the XRPD patterns of a 96:4 (by weight) mixture of hydrated lanthanum carbonate/D-mannitol at 60° C./95% RH for 0, 1, 2, 3, 4, 7, and 14 days.

6.5.2.11 The Stabilization of Hydrated Lanthanum Carbonate in a 96:4 (by Weight) Hydrated Lanthanum Carbonate/D-Mannitol Mixture A study of a 96:4 (by weight) hydrated lanthanum carbonate/D-mannitol mixture was performed using the methods described above. This mixture was stressed at 60° C. and 95% relative humidity for 14 days. The results are summarized in FIG. 14.

After 7 days of stressing, no decarboxylation of the hydrated lanthanum carbonate in the mixture was detected. After 14 days of stressing, only a trace amount of decarboxylation of the hydrated lanthanum carbonate in the mixture was detected.

6.5.3. Conclusions

The results show that mono- and disaccharides, such as mannitol, sorbitol, lactose and dextrates, offer a stabilizing protection to formulations containing lanthanum carbonate (anhydrous and hydrated) in reducing or eliminating the decarboxylation to lanthanum hydroxycarbonate. Polysaccharides such as corn starch, beta-cyclodextrins and microcrystalline cellulose, do not offer such protection and so decarboxylation was seen in formulations containing such materials at a similar rate to the unformulated drug substance exposed to the same conditions.

6.6. Example 6

Decarboxylation Rates of Hydrated Lanthanum Carbonate Under Ambient Conditions

Unformulated hydrated lanthanum carbonate and formulated hydrated lanthanum carbonate tablets containing approximately 50% (by weight) dextrates were exposed to the standard ICH stability conditions of 25° C./60% RH, 30° C./60% RH and 40° C./75% RH for a period up to 2 years. Samples were removed periodically over this time and tested for their lanthanum hydroxycarbonate content using x-ray powder diffraction.

Figure 15:
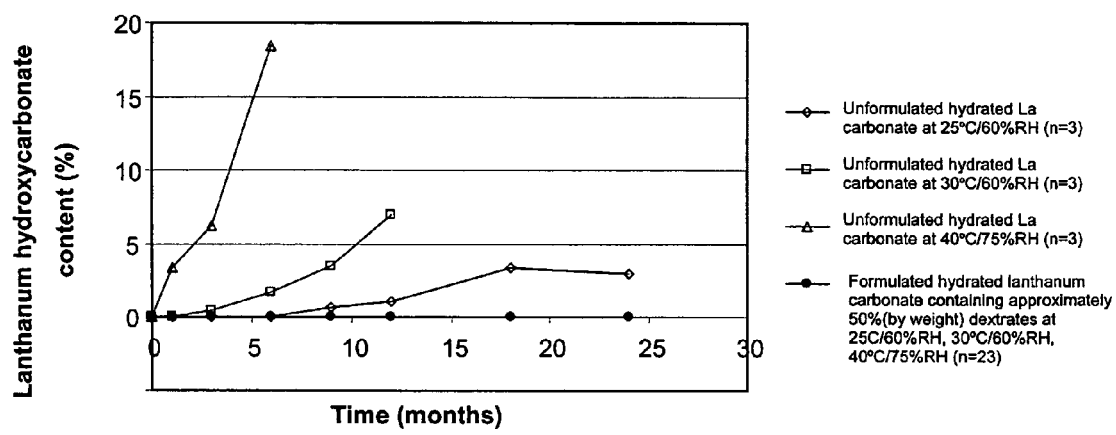
FIG. 15 shows the degradation to lanthanum hydroxycarbonate that occurs in unformulated hydrated lanthanum carbonate and formulated hydrated lanthanum carbonate containing approximately 50% (by weight) dextrates at 25° C./60% RH, 300C/60% RH, and 40° C./75% RH for up to 24 months.

FIG. 15 shows the decarboxylation rates of unformulated hydrated lanthanum carbonate and demonstrates significant degradation of the unformulated hydrated lanthanum carbonate at the standard ICH stability conditions of 25° C./60% RH, 30° C./60% RH and 40° C./75% RH. The degradation at the 25° C./60% RH condition results indicates the need to store the unformulated drug substance in refrigerated conditions in order to slow the degradation rate. In contrast, no decarboxylation can be detected in similarly stored tablets formulated with about 50% (by weight) dextrates as shown in FIG. 15.

This experiment demonstrates that the dextrates are stabilizing the hydrated lanthanum carbonate by preventing decarboxylation at standard ambient conditions.

The present invention is not to be limited in scope by the specific embodiments described herein. Indeed, various modifications of the invention in addition to those described herein will be apparent to those skilled in the art from the foregoing description. Such modifications are intended to fall within the scope of the appended claims.

All references cited herein, including all patents, published patent applications, and published scientific articles and books, are incorporated by reference in their entireties for all purposes.

What is claimed is:

1. In a method for treating hyperphosphatemia comprising administering a therapeutically effective amount of a lanthanum carbonate composition comprising lanthanum carbonate having the formula:

$$La_2(CO_3)_3 \cdot xH_2O$$

wherein x has a value from 0 to 10, in an amount effective to treat hyperphosphatemia, the improvement comprising: stabilizing the lanthanum carbonate against substantial decarboxylation to lanthanum hydroxycarbonate before administration by admixing the lanthanum carbonate in an amount of from 13.4-13.9% to 32.2-33.3% by weight of the composition as elemental lanthanum with a monosaccharide or disaccharide in an amount from 20 to 80% by weight of the composition, wherein the monosaccharide or disaccharide is dextrates, mannitol, sorbitol, or a mixture thereof and the amount of the monosaccharide or disaccharide is such that lanthanum hydroxycarbonate is not observed in an x-ray powder diffraction (XRPD) pattern of the lanthanum carbonate composition after it has been exposed to 60° C. and 95% relative humidity for at least 7 days.

2. The method of claim 1, wherein the monosaccharide or disaccharide is dextrates.

3. The method of claim 1, wherein the monosaccharide or disaccharide is sorbitol.

4. The method of claim 1, wherein the stabilized composition comprises 26.5% by weight lanthanum carbonate, 69.3% by weight dextrates, 2% by weight colloidal silicon dioxide, 1.7% by weight talc, and 0.5% by weight magnesium stearate, and wherein the lanthanum carbonate has a water content approximately equivalent to 4-5 moles of water.

5. The method of claim 1, wherein the stabilized composition comprises 63.6% by weight lanthanum carbonate, 2% by weight colloidal silicon dioxide, 1% by weight talc, 30.4% by weight sorbitol, and 3.0% by weight glyceryl dibehenate, and wherein the lanthanum carbonate has a water content approximately equivalent to 4-5 moles of water.

6. The method of claim 1, wherein the stabilized composition comprises 45.8% by weight lanthanum carbonate, 51.1% by weight dextrates, 2.1% by weight colloidal silicon dioxide, and 1.0% by weight magnesium stearate, and wherein the lanthanum carbonate has a water content approximately equivalent to 4-5 moles of water.

7. A method for stabilizing a lanthanum carbonate pharmaceutical composition for treating hyperphosphatemia, the lanthanum carbonate having the formula:

$$La_2(CO_3)_3 \cdot xH_2O$$

wherein x has a value from 0 to 10, and the lanthanum carbonate being stabilized against substantial decarboxylation to lanthanum hydroxycarbonate comprising:
admixing the lanthanum carbonate in an amount of from 13.4-13.9% to 32.2-33.3% by weight of the composition as elemental lanthanum with a monosaccharide or disaccharide in an amount from 20 to 80% by weight of the composition, wherein the monosaccharide or disaccharide is dextrates, mannitol, sorbitol, or a mixture thereof and the amount of the monosaccharide or disaccharide is such that lanthanum hydroxycarbonate is not observed in an x-ray powder diffraction (XRPD) pattern of the lanthanum carbonate composition after it has been exposed to 60° C. and 95% relative humidity for at least 7 days.

8. The method of claim 7, wherein the monosaccharide or disaccharide is dextrates.

9. The method of claim 7, wherein the monosaccharide or disaccharide is sorbitol.

10. The method of claim 7, wherein the stabilized composition comprises 26.5% by weight lanthanum carbonate, 69.3% by weight dextrates, 2% by weight colloidal silicon dioxide, 1.7% by weight talc, and 0.5% by weight magnesium stearate, and wherein the lanthanum carbonate has a water content approximately equivalent to 4-5 moles of water.

11. The method of claim 7, wherein the stabilized composition comprises 63.6% by weight lanthanum carbonate, 2% by weight colloidal silicon dioxide, 1% by weight talc, 30.4% by weight sorbitol, and 3.0% by weight glyceryl dibehenate, and wherein the lanthanum carbonate has a water content approximately equivalent to 4-5 moles of water.

12. The method of claim 7, wherein the stabilized composition comprises 45.8% by weight lanthanum carbonate, 51.1% by weight dextrates, 2.1% by weight colloidal silicon dioxide, and 1.0% by weight magnesium stearate, and wherein the lanthanum carbonate is hydrated having a water content approximately equivalent to 4-5 moles of water.

* * * * *